(12) United States Patent
Stadtmueller et al.

(10) Patent No.: US 7,569,561 B2
(45) Date of Patent: Aug. 4, 2009

(54) 2,4-DIAMINOPYRIMIDINES USEFUL FOR TREATING CELL PROLIFERATION DISEASES

(75) Inventors: Heinz Stadtmueller, Vienna (AT); Anke Baum, Vienna (AT); Guido Boehmelt, Gaaden (AT); Harald Engelhardt, Ebreichsdorf (AT); Jens Juergen Quant, Perchtoldsdorf (AT); Flavio Solca, Vienna (AT); Martin Steegmaier, Reutlingen (DE); Stephan Karl Zahn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 292 days.

(21) Appl. No.: 11/675,936

(22) Filed: Feb. 16, 2007

(65) Prior Publication Data

US 2007/0207999 A1 Sep. 6, 2007

(30) Foreign Application Priority Data

Feb. 22, 2006 (EP) .................. 06110303

(51) Int. Cl.
| | |
|---|---|
| C07D 403/12 | (2006.01) |
| C07D 413/12 | (2006.01) |
| C07D 498/04 | (2006.01) |
| C07D 487/04 | (2006.01) |
| A61K 31/551 | (2006.01) |
| A61K 31/553 | (2006.01) |
| A61P 29/00 | (2006.01) |
| A61P 35/00 | (2006.01) |
| A61P 37/00 | (2006.01) |

(52) U.S. Cl. .................. 514/211.04; 514/211.05; 514/220; 514/221; 540/488; 540/490; 540/495; 540/496; 540/506

(58) Field of Classification Search ............ 514/211.04, 514/211.05, 220, 221; 540/488, 490, 495, 540/496, 506
See application file for complete search history.

(56) References Cited

FOREIGN PATENT DOCUMENTS

| WO | 2004/074244 A2 | 9/2004 |
| WO | 2004/080980 A1 | 9/2004 |
| WO | 2006/021544 A1 | 3/2006 |

OTHER PUBLICATIONS

ISR—PCT/EP2007/051599, (2007).
G. Wolf, et al., "Prognostic significance of polo-like kinase (PLK) expression in non-small cell lung cancer", Oncogene, 1997, vol. 14, p. 543.
J. P. H. Th'ng, et al., "The FT210 Cell Line is a Mouse G2 Phase Mutant with a Temperature-Sensitive CDC2 Gene Product", Cell, vol. 63, p. 313, 1990.
T. Takahashi, et al., "Polo-like kinase 1 (PLK1) is overexpressed in primary colorectal cancers", Cancer Sci, 2003, vol. 94, No. 2, p. 148.
P. B. Schiff, et al., "Taxol stabilizes microtubules in mouse fibroblast cells", Proc. Natl. Acad. Sci. USA, vol. 77, No. 3, pp. 1561, 1980.
P. Russell, et al., "Negative Regulation of Mitosis by wee1, a Gene Encoding a Protein Kinase Homolog", Cell, vol. 49, p. 559, 1987.
P. Russell, et al., "cdc25 Functions as an Inducer in the Mitotic Control of Fission Yeast", Cell, vol. 45, p. 145, 1986.
Y-W Qian, et al., "The Polo-like Kinase P1x1 Is Required for Activation of the Phosphatase Cdc25C and Cyclin B-Cdc2 in Xenopus Oocytes", Molecular Biol of the Cell, vol. 12, p. 1791, 2001.
P. Nurse, "Universal control mechanism regulating onset of M-phase", Nature, vol. 344, 1990, pp. 503.
T.U. Mayer, et al., "Small Molecule Inhibitor of Mitotic Spindle Bipolarity Identified in a Phenotype-Based Screen", Science, vol. 286, p. 971, 1999.
X. Liu, et al., "Polo-like kinase (PLK)1 depletion induces apoptosis in cancer cells", PNAS, vol. 100, No. 10, p. 5789, 2003.
H.A. Lane, et al., "Antibody Microinjection Reveals an Essential Role for Human Polo-like Kinase 1 (PLK1) in the Functional Maturation of Mitotic Centrosomes". J. Cell Biology, vol. 135. No. 6. part2, p. 1701, 1996.
R. Knecht, et al., "Prognostic Significance of Polo-like Kinase (PLK) Expression in Squamous Cell Carcinomas of the Head and Neck", Cancer Research, vol. 59, p. 2794, 1999.

(Continued)

Primary Examiner—Bruck Kifle
(74) Attorney, Agent, or Firm—Michael P. Morris; Mary-Ellen M. Devlin; Anthony P. Bottino

(57) ABSTRACT

The present invention encompasses compounds of general formula (1)

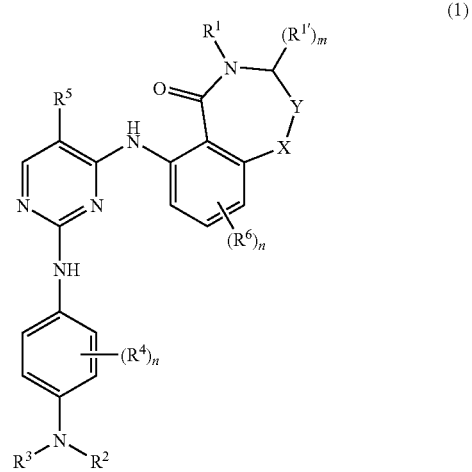

(1)

wherein
$R^1$ to $R^6$, X and Y are defined as in claim 1, which are suitable for the treatment of diseases characterised by excessive or anomalous cell proliferation, as well as the use thereof for preparing a pharmaceutical composition with the above-mentioned properties.

8 Claims, No Drawings

OTHER PUBLICATIONS

J-Y Hsu, et al., "Mitotic Phosphorylation of Histone H3 is Governed by Ipl1/aurora Kinase and Glc7/pp1 Phosphatase in Budding Yeast and Nematodes", Cell, vol. 102, p. 279, 2000.

D.M. Glover, et al., "Polo-like Kinases: a team that plays throughout mitosis", Genes & Development, vol. 12, p. 3777, 1998.

G. Wolf, et al., "Polo-like Kinase: a Novel Marker of Proliferation: Correlation with Estrogen-receptor Expression in Human Breast Cancer", Pathology Res. Pract. vol. 196, p. 753, 2000.

K. Nishio, et al., "Antitumor Effects of Butyrolactone I, a Selective cdc2 Kinase Inhibitor, on Human Lunch Cancer Cell Lines", Anticancer Research, vol. 16, p. 3387, 1996.

E. Nigg, "Mitotic Kinases as Regulators of Cell Division and Its Checkpoints", Nature Reviews / Molecular Cell Biology, vol. 2, p. 21, 2001.

ISA 237 Written Opinion—PCT/EP2007/051599 Translation, (2007).

2,4-DIAMINOPYRIMIDINES USEFUL FOR TREATING CELL PROLIFERATION DISEASES

This application claims priority benefit of EP 06 110 303, filed Feb. 22, 2006, which is incorporated herein in its entirety.

The present invention relates to new 2,4-diaminopyrimidines of general formula (1)

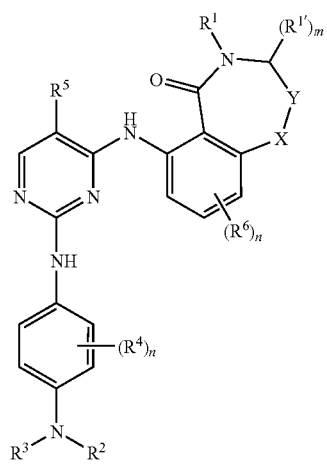

wherein the groups $R^1$ to $R^6$, X and Y have the meanings given in the claims and specification, the isomers thereof, processes for preparing these pyrimidines and their use as pharmaceutical compositions.

BACKGROUND TO THE INVENTION

Tumour cells wholly or partly elude regulation and control by the body and are characterised by uncontrolled growth. This is due on the one hand to the loss of control proteins such as for example Rb, p16, p21 and p53 and also to the activation of so-called accelerators of the cell cycle, the cyclin-dependent kinases.

Studies in model organisms such as *Schizosaccharomyces pombe*, *Drosophila melanogaster* or *Xenopus laevis* as well as investigations in human cells have shown that the transition from the G2 phase to mitosis is regulated by the CDK1/cyclin B kinase (Nurse 1990, *Nature* 344: 503-508). This kinase, which is also known as "mitosis promoting factor" (MPF), phosphorylates and thereby regulates a plurality of proteins, such as e.g. nuclear lamina, kinesin-like motor proteins, condensins and Golgi Matrix Proteins, which play an important part in the breakdown of the nuclear coat, in centrosome separation, the structure of the mitotic spindle apparatus, chromosome condensation and breakdown of the Golgi apparatus (Nigg. E. 2001, *Nat Rev Mol Cell Biol.* 2(1):21-32). A murine cell line with a temperature-sensitive CDK-1 kinase mutant shows a rapid breakdown in CDK-1 kinase after temperature increase and a subsequent arrest in the G2/M phase (Th'ng et al., 1990, *Cell.* 63(2):313-24). The treatment of human tumour cells with inhibitors against CDK1/cyclin B, such as e.g. butyrolactone, leads to an arrest in the G2/M phase and subsequent apoptosis (Nishio, et al. 1996, *Anticancer Res.* 16(6B):3387-95).

Moreover, the protein kinase Aurora B has also been described as having an essential function during entry into mitosis. Aurora B phosphorylates histone H3 on Ser10 and thereby initiates chromosome condensation (Hsu et al. 2000, *Cell* 102:279-91). A specific cell cycle arrest in the G2/M phase may, however, also be initiated e.g. by inhibition of specific phosphatases such as e.g. Cdc25C (Russell and Nurse 1986, *Cell* 45:145-53). Yeasts with a defective Cdc25 gene arrest in the G2 phase, whereas overexpression of Cdc25 leads to premature entry into the mitosis phase (Russell and Nurse, 1987, *Cell* 49:559-67). Moreover, an arrest in the G2/M phase may also be initiated by inhibition of specific motor proteins, the so-called kinesins such as for example Eg5 (Mayer et al., 1999, *Science* 286:971-4)), or by microtubuli stabilising or destabilising agents (e.g. colchicin, taxol, etoposide, vinblastine, vincristine) (Schiff and Horwitz 1980, *Proc Natl Acad Sci USA* 77:1561-5).

In addition to the cyclin-dependent and Aurora kinases the so-called polo-like kinases (PLK), a small family of serine/threonine kinases, also play an important role in the regulation of the eukaryotic cell cycle. Hitherto, the polo-like kinases PLK-1, PLK-2, PLK-3 and PLK-4 have been described in the literature. PLK-1 in particular has been found to play a central role in the regulation of the mitosis phase. PLK-1 is responsible for the maturation of the centrosomes, for the activation of phosphatase Cdc25C, as well as for the activation of the Anaphase Promoting Complex (Glover et al. 1998, *Genes Dev.* 12:3777-87; Qian et al. 2001, *Mol Biol Cell.* 12:1791-9). The injection of PLK-1 antibodies leads to a G2 arrest in untransformed cells, whereas tumour cells arrest during the mitosis phase (Lane and Nigg 1996, *J Cell Biol.* 135:1701-13). Overexpression of PLK-1 has been demonstrated in various types of tumour, such as non-small-cell carcinoma of the lung, plate epithelial carcinoma, breast and colorectal carcinoma (Wolf et al. 1997, *Oncogene* 14:543-549; Knecht et al. 1999, *Cancer Res.* 59:2794-2797; Wolf et al. 2000, *Pathol. Res. Pract.* 196:753-759; Takahashi et al. 2003, *Cancer Sci.* 94:148-52). Therefore, this category of proteins also presents an interesting point of attack for therapeutic intervention in proliferative diseases (Liu and Erikson 2003, *Proc Natl Acad Sci USA* 100:5789-5794).

The resistance of many types of tumours requires the development of new drugs for combating tumours. The aim of the present invention is therefore to indicate new active substances which may be used for the prevention and/or treatment of diseases characterised by excessive or anomalous cell proliferation.

DETAILED DESCRIPTION OF THE INVENTION

It has now been found that, surprisingly, compounds of general formula (1), wherein the groups $R^1$ to $R^6$, X and Y are defined as hereinafter, act as inhibitors of specific cell cycle kinases. Thus, the compounds according to the invention may be used for example for the treatment of diseases associated with the activity of specific cell cycle kinases and characterised by excessive or anomalous cell proliferation.

The present invention relates to compounds of general formula (1)

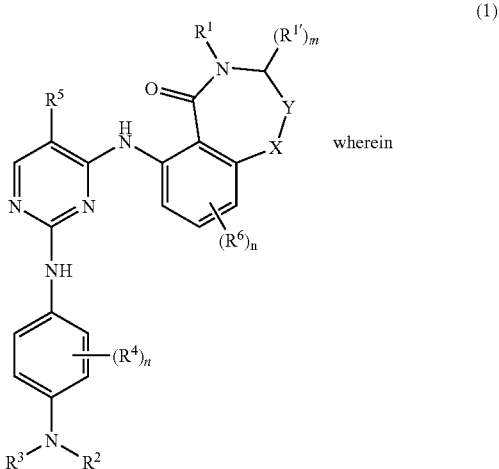

wherein

X denotes oxygen or nitrogen, and

Y denotes —$CH_2$ or C=O, and $R^1$ and $R^{1'}$ each independently of one another denote hydrogen or an optionally mono- or polysubstituted group selected from among $C_{1-5}$-alkyl, $C_{3-6}$-cycloalkyl, aryl, heterocyclyl and heteroaryl, wherein the substituent(s) may be identical or different and are selected from among halogen, —$OR^a$, —C(=O)$R^a$, —C(=O)$OR^a$, —C(=O)$NR^aR^a$, —$NR^aR^a$, —$NR^aC$(=O)$R^a$, —$NR^aC$(=O)$OR^a$, —$NR^aC$(=O)$NR^aR^a$, —$NR^aSO_2R^a$, —N=$CR^aR^a$, —$SR^a$, —$SOR^a$, —$SO_2R^a$, —$SO_2NR^aR^a$, —$NR^aSO_2NR^aR^a$, —$OSO_2NR^aR^a$ and pseudohalogen, or optionally two $R^{1'}$ groups on the same carbon atom may together with the carbon atom to which they are attached form a $C_{3-7}$ cycloalkyl ring, or optionally $R^1$ may together with an $R^{1'}$ group form a saturated or partly saturated 3-6 membered alkyl bridge, which may optionally contain one to two heteroatoms, and $R^2$ denotes an optionally mono- or polysubstituted heterocyclyl group, wherein the substituent(s) may be identical or different and are selected from among $C_{1-5}$-alkyl, $C_{2-5}$-alkenyl, $C_{2-5}$-alkynyl, $C_{3-6}$-cycloalkyl-$C_{0-3}$-alkyl, and $R^3$ denotes hydrogen or $C_{1-3}$-alkyl, or $R^2$ and $R^3$ together form an optionally mono- or polysubstituted heterocyclyl ring, which may optionally contain one to two further heteroatoms, wherein the substituent(s) may be identical or different and are selected from among $C_{1-5}$-alkyl, $C_{2-5}$-alkenyl, $C_{2-5}$-alkynyl and $C_{3-6}$-cycloalkyl-$C_{0-3}$-alkyl, or a suitable substituent selected from among halogen, —$OR^a$, —C(=O)$R^a$, —C(=O)$OR^a$, —C(=O)$NR^aR^a$, —$NR^aR^a$, —$NR^aC$(=O)$R^a$, —$NR^aC$(=O)$OR^a$, —$NR^aC$(=O)$NR^aR^a$, —$NR^aSO_2R^a$, —N=$CR^aR^a$, —$SR^a$, —$SOR^a$, —$SO_2R^a$, —$SO_2NR^aR^a$, —$NR^aSO_2NR^aR^a$, —$OSO_2NR^aR^a$ and pseudohalogen, and $R^4$ each independently of one another denote a group selected from among halogen, $NO_2$, —$OR^a$, —C(=O)$R^a$, —C(=O)$OR^a$, —C(=O)$NR^aR^a$, —$NR^aR^a$, —$NR^a$COR$^a$, —$NR^aC$(=O)$OR^a$, —$NR^aC$(=O)$NR^aR^a$, —$NR^aC$(=O)$ONR^aR^a$, —$NR^aSO_2R^a$, —N=$CR^aR^a$, —$SR^a$, —$SOR^a$, —$SO_2R^a$, —$SO_2NR^aR^a$, —$NR^aSO_2NR^aR^a$, —$OSO_2NR^aR^a$ and pseudohalogen; and $R^5$ denotes hydrogen, halogen, $C_{1-3}$-alkyl, $C_{2-3}$-alkenyl, $C_{2-3}$-alkynyl, halogen-$C_{1-3}$-alkyl, —$OR^a$ or pseudohalogen, and $R^6$ each independently of one another denote a group selected from among halogen, $C_{1-3}$-alkyl, —$OR^a$ and pseudohalogen, and $R^a$ each independently of one another denote hydrogen or a group selected from among optionally substituted $C_{1-8}$-alkyl, $C_{2-8}$-alkenyl, $C_{2-8}$-alkynyl, $C_{3-10}$-cycloalkyl, aryl, heterocyclyl and heteroaryl, while the substituent(s) may be identical or different and are selected from among halogen, —$NH_2$, —OH and pseudohalogen; and m denotes 0, 1 or 2; and n each independently of one another denote 0, 1 or 2 optionally in the form of the tautomers, the racemates, the enantiomers, the diastereomers and the mixtures thereof, as well as optionally the pharmacologically acceptable salts thereof, with the proviso that 2-(2-methoxy-4-piperazin-1-yl-phenylamino)-4-(3,3-dimethyl-5-oxo-2,3,4,5-benzo[f][1,4]oxazepin-6-ylamino-5-trifluoromethyl-pyrimidine, 2-(2-methoxy-4-piperazin-1-yl-phenylamino)-4-((S)-4-oxo-2,3,10,10a-tetrahydro-1H,4H-9-oxa-3a-aza-benzo[f]azulen-5-ylamino-5-trifluoromethyl-pyrimidine, 2-[4-(4-ethyl-piperazin-1-yl)-2-methoxy-phenylamino]-4-((S)-4-oxo-2,3,10,10a-tetrahydro-1H,4H-9-oxa-3a-aza-benzo[f]azulen-5-ylamino-5-trifluoromethyl-pyrimidine, 2-[4-(4-methyl-piperazin-1-yl)-2-methoxy-phenylamino]-4-((S)-4-oxo-2,3,10,10a-tetrahydro-1H,4H-9-oxa-3a-aza-benzo[f]azulen-5-ylamino-5-trifluoromethyl-pyrimidine, 3,3-dimethyl-6-{2-[4-(4-methyl-piperazin-1-yl)-phenylamino]-5-trifluoromethyl-pyrimidin-4-ylamino}-3,4-dihydro-2H-benzo[f][1,4]oxazepin-5-one, 6-{2-[4-(4-ethyl-piperazin-1-yl)-phenylamino]-5-trifluoromethyl-pyrimidin-4-ylamino}-3,3-dimethyl-3,4-dihydro-2H-benzo[f][1,4]oxazepin-5-one, 3,3-dimethyl-6-{2-[4-(4-prop-2-ynyl-piperazin-1-yl)-phenylamino]-5-trifluoromethyl-pyrimidin-4-ylamino}-3,4-dihydro-2H-benzo[f][1,4]oxazepin-5-one, 6-{2-[4-(4-isopropyl-piperazin-1-yl)-phenylamino]-5-trifluoromethyl-pyrimidin-4-ylamino}-3,3-dimethyl-3,4-dihydro-2H-benzo[f][1,4]oxazepin-5-one, (S)-3-methyl-6-[2-(4-piperazin-1-yl-phenylamino)-5-trifluoromethyl-pyrimidin-4-ylamino]-3,4-dihydro-2H-benzo[f][1,4]oxazepin-5-one, (S)-3-methyl-6-{2-[4-(4-methyl-piperazin-1-yl)-phenylamino]-5-trifluoromethyl-pyrimidin-4-ylamino}-3,4-dihydro-2H-benzo[f][1,4]oxazepin-5-one, (S)-6-{2-[4-(4-isopropyl-piperazin-1-yl)-phenylamino]-5-trifluoromethyl-pyrimidin-4-ylamino}-3-methyl-3,4-dihydro-2H-benzo[f][1,4]oxazepin-5-one, (S)-3-methyl-6-{2-[4-(4-prop-2-ynyl-piperazin-1-yl)-phenylamino]-5-trifluoromethyl-pyrimidin-4-ylamino}-3,4-dihydro-2H-benzo[f][1,4]oxazepin-5-one, (S)-3-ethyl-6-[2-(4-piperazin-1-yl-phenylamino)-5-trifluoromethyl-pyrimidin-4-ylamino]-3,4-dihydro-2H-benzo[f][1,4]oxazepin-5-one, (S)-6-[2-(4-piperazin-1-yl-phenylamino)-5-trifluoromethyl-pyrimidin-4-ylamino]-3-propyl-3,4-dihydro-2H-benzo[f][1,4]oxazepin-5-one, (S)-6-{2-[4-(4-prop-2-ynyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-ethyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-isobutyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-methyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, 6-{2-[4-(4-ethyl-piperazin-1-yl)-phenylamino]-5-trifluoromethyl-pyrimidin-4-ylamino}-3,3-dimethyl-3,4-dihydro-1H-benzo[e][1,4]diazepine-2,5-dione, 3,3-dimethyl-6-{2-[4-(4-methyl-piperazin-1-yl)-phenylamino]-5-trifluoromethyl-pyrimidin-4-ylamino}-3,4-dihydro-1H-benzo[e][1,4]diazepine-2,5-dione, 6-{2-[4-(4-isopropyl-piperazin-1-yl)-phenylamino]-5-trifluoromethyl-pyrimidin-4-ylamino}-3,3-dimethyl-3,4-dihydro-1H-benzo[e][1,4]diazepine-2,5-dione, 3,3-dimethyl-6-{2-[4-(4-prop-2-ynyl-piperazin-1-yl)-phenylamino]-5-trifluoromethyl-pyrimidin-4-ylamino}-3,4-dihydro-1H-benzo[e][1,4]diazepine-2,5-dione, (S)-6-{2-[4-(4-isopropyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-isopropyl-piperazin-1-yl)-phenylamino]-5-trifluoromethyl-pyrimidin-4-ylamino}-3-methyl-3,4-dihydro-1H-benzo[e][1,4]diazepine-2,5-dione, (S)-3-methyl-6-{2-[4-(4-methyl-piperazin-1-yl)-phenylamino]-5-trifluoromethyl-pyrimidin-4-ylamino}-3,4-dihydro-1H-benzo[e][1,4]diazepine-2,5-dione, (S)-3-methyl-6-{2-[4-(4-prop-2-ynyl-piperazin-1-yl)-phenylamino]-5-trifluoromethyl-pyrimidin-4-ylamino}-3,4-dihydro-1H-benzo[e][1,4]diazepine-2,5-dione, (S)-6-{2-[4-(4-ethyl-piperazin-1-yl)-phenylamino]-5-trifluoromethyl-pyrimidin-4-ylamino}-3-methyl-3,4-dihydro-1H-benzo[e][1,4]diazepine-2,5-dione and methyl {(S)-2,5-dioxo-6-[2-(4-piperazin-1-yl-phenylamino)-5-trifluoromethyl-pyrimidin-4-ylamino]-2,3,4,5-tetrahydro-1H-benzo[e][1,4]diazepin-3-yl}-acetate are excluded.

In one aspect the invention relates to compounds of general formula (1), wherein $R^5$ denotes halogen or $-CF_3$.

In another aspect the invention relates to compounds of general formula (1), wherein
X denotes oxygen and
Y denotes $-CH_2-$.

In another aspect the invention relates to compounds of general formula (1), wherein
X denotes nitrogen and
Y denotes C=O.

(A) Aspects Relating to $R^{1'}$ (A1) In one aspect the invention relates to compounds of general formula (1), wherein $R^{1'}$ denotes $C_{1-5}$-alkyl and m=1.

(A2) In one aspect the invention relates to compounds of general formula (1), wherein $R^{1'}$ denotes $C_{1-5}$-alkyl and m=2.

(A3) In one aspect the invention relates to compounds of general formula (1), wherein the two $R^{1'}$ together form a cycloalkyl group.

(A4) In another aspect the invention relates to compounds of general formula (1), wherein $R^1$ with an $R^{1'}$ forms a cyclopentyl ring.

(B) Aspects Relating to $R^2$ and $R^3$ (B1) In one aspect the invention relates to compounds of general formula (1), wherein $R^2$ denotes an optionally monosubstituted piperidinyl group.

(B2) In another aspect the invention relates to compounds of general formula (1), wherein $R^2$ denotes a piperidinyl group substituted at the nitrogen.

(B3) In another aspect the invention relates to compounds of general formula (1), wherein $R^2$ denotes a piperidinyl group substituted at the nitrogen by methyl, ethyl or cyclopropylmethyl.

(B4) In another aspect the invention relates to compounds of general formula (1), wherein $R^2$ and $R^3$ together form an optionally mono- or polysubstituted piperazinyl group.

(B5) In another aspect the invention relates to compounds of general formula (1), wherein $R^2$ and $R^3$ together denote a piperazinyl group substituted at the nitrogen.

(B6) In another aspect the invention relates to compounds of general formula (1), wherein $R^2$ and $R^3$ together represent a piperazinyl group substituted at the nitrogen by methyl, ethyl, isopropyl or cyclopropylmethyl.

(C) Aspects Relating to X and Y (C1) In one aspect the invention relates to compounds of general formula (1), wherein X denotes oxygen and Y $-CH_2-$.

(C2) In another aspect the invention relates to compounds of general formula (1), wherein X denotes nitrogen and Y denotes C=O.

All the above-mentioned aspects (A1) to (A4) for $R^{1'}$, (B1) to (B6) for $R^2$ and $R^3$ and (C1) and (C2) for X and Y may be combined with one another as desired.

The Table that follows lists preferred combinations of various aspects of the novel compounds of formula (1):

| embodiment | $R^{1'}$ | $R^2$ and $R^3$ | X and Y |
|---|---|---|---|
| I-1  | A1 | B1 | C1 |
| I-2  | A1 | B2 | C1 |
| I-3  | A1 | B3 | C1 |
| I-4  | A1 | B4 | C1 |
| I-5  | A1 | B5 | C1 |
| I-6  | A1 | B6 | C1 |
| I-7  | A2 | B4 | C1 |
| I-8  | A2 | B5 | C1 |
| I-9  | A2 | B6 | C1 |
| I-10 | A3 | B4 | C2 |
| I-11 | A4 | B4 | C1 |
| I-12 | A4 | B5 | C1 |
| I-13 | A4 | B6 | C1 |
| I-14 | A4 | B4 | C2 |
| I-15 | A4 | B5 | C2 |
| I-16 | A4 | B6 | C2 |

In another aspect the invention relates to compounds of general formula (1)—or the pharmacologically acceptable salts thereof—as pharmaceutical compositions.

In another aspect the invention relates to compounds of general formula (1)—or the pharmacologically acceptable salts thereof—for preparing a pharmaceutical composition with an antiproliferative activity.

In another aspect the invention relates to compounds of general formula (1)—or the pharmacologically acceptable salts thereof—for preparing a pharmaceutical composition with an antiproliferative activity with a selective kinase-inhibiting mechanism of activity.

In another aspect the invention relates to the use of a compound of general formula 1 for preparing a pharmaceutical composition for the treatment and/or prevention of cancer, infections, inflammatory and autoimmune diseases.

In another aspect the invention relates to a pharmaceutical preparation, containing as active substance one or more compounds of general formula (1), or the pharmacologically acceptable salts thereof, optionally in combination with conventional excipients and/or carriers.

In another aspect the invention relates to a pharmaceutical preparation containing a compound of general formula (1), optionally in the form of the tautomers, the racemates, the enantiomers, the diastereomers and the mixtures thereof, as well as optionally the pharmacologically acceptable acid addition salts thereof, and at least one other active cytostatic or cytotoxic active substance.

Definitions

As used herein the following definitions apply, unless otherwise stated.

By alkyl substituents are meant in each case saturated, unsaturated, straight-chain or branched aliphatic hydrocarbon groups (alkyl group) and the definition includes both saturated alkyl groups and unsaturated alkenyl and alkynyl groups. Alkenyl substituents are in each case straight-chain or branched, unsaturated alkyl groups which have at least one double bond. By alkynyl substituents are meant in each case straight-chain or branched, unsaturated alkyl groups which have at least one triple bond.

Heteroalkyl denotes straight-chain or branched aliphatic hydrocarbon chains which contain 1 to 3 heteroatoms, while each of the available carbon and heteroatoms in the heteroalkyl chain may each optionally be substituted independently of one another and the heteroatoms are selected independently of one another from the group consisting of O, N, P, PO, $PO_2$, S, SO and $SO_2$ (e.g. dimethylaminomethyl, dimethylaminoethyl, dimethylaminopropyl, diethylaminomethyl, diethylaminoethyl, diethylaminopropyl, 2-diisopropylaminoethyl, bis-2-methoxyethylamino, [2-(dimethylaminoethyl)-ethyl-amino]-methyl, 3-[2-(dimethylamino-ethyl)-ethyl-amino]-propyl, hydroxymethyl, 2-hydroxyethyl, 3-hydroxypropyl, methoxy, ethoxy, propoxy, methoxymethyl, 2-methoxyethyl).

Halogen refers to fluorine, chlorine, bromine and/or iodine atoms.

Haloalkyl refers to alkyl groups wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CJ=$CH_2$, —C≡C—$CF_3$, —$CHFCH_2CH_3$ and —$CHFCH_2CF_3$.

By pseudohalogen are meant the following groups: —OCN, —SCN, —CF3 and —CN.

By cycloalkyl is meant a mono- or polycyclic ring, wherein the ring system may be a saturated ring but also an unsaturated, non-aromatic ring or a spiro compound, which may optionally also contain double bonds, such as for example cyclopropyl, cyclopropenyl, cyclobutyl, cyclobutenyl, cyclopentyl, cyclopentenyl, cyclohexyl, cyclohexenyl, cycloheptanyl, cycloheptenyl, norbornyl, norbornenyl, indanyl, adamantyl, spiroheptanyl and spiro[4,2]heptanyl.

Cycloalkylalkyl includes a non-cyclic alkyl group wherein a hydrogen atom bound to a carbon atom is replaced by a cycloalkyl group.

Aryl relates to monocyclic or bicyclic rings with 6-12 carbon atoms such as for example phenyl and naphthyl.

Arylalkyl includes a non-cyclic alkyl group wherein a hydrogen atom bound to a carbon atom is replaced by an aryl group.

By heteroaryl are meant mono- or polycyclic rings which contain, instead of one or more carbon atoms, one or more heteroatoms, which may be identical or different, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom is replaced by a heteroaryl group.

Heterocyclyl relates to saturated or unsaturated, non-aromatic mono-, polycyclic or bridged polycyclic rings or spiro compounds comprising 3-12 carbon atoms, which carry heteroatoms, such as nitrogen, oxygen or sulphur, instead of one or more carbon atoms. Examples of such heterocyclyl groups are tetrahydrofuranyl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane.

Heterocycloalkylalkyl relates to a non-cyclic alkyl group wherein a hydrogen atom bound to a carbon atom is replaced by a heterocycloalkyl group.

Preparation of the Compounds According to the Invention

The compounds according to the invention may be prepared according to the methods of synthesis A or B described in the following text, wherein the substituents of general formulae (I to VI) have the meanings stated above. The compounds used as starting materials are known from the literature in some cases or are obtained by methods known from the literature. These methods are to be understood as being an explanation of the invention, without restricting it to their content.

Method A

Step 1A

The intermediate compound III is prepared by substitution of a leaving group LG, for example halogen, SCN or methoxy, preferably chlorine, at a heteroaromatic system I by a nucleophile II.

Diagram 1A

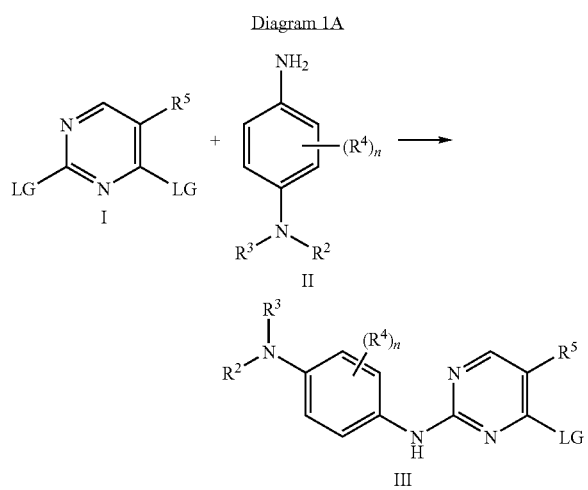

1 equivalent of compound I and 1 to 1.5 equivalents of compound II are stirred in a solvent, for example 1,4-dioxane, tetrahydrofuran, N,N-dimethylformamide or N,N-dimethylacetamide. At a temperature of 15 to 25° C., 2 to 2.5 equivalents of a base, for example potassium carbonate, sodium carbonate, caesium carbonate, N-ethyl-N,N-diisopropylamine or triethylamine are added. The reaction mixture is stirred for 12 to 72 h at a temperature of 15 to 25° C. Then the solvent is distilled off and the residue is mixed with water which is adjusted to an acid pH of less than 4 with an inorganic acid such as hydrochloric acid or sulphuric acid. This mixture is extracted twice or three times with an organic solvent, such as for example diethyl ether, ethyl acetate or dichloromethane. The combined organic extracts are dried and the solvent is distilled off. The residue is purified by chromatography.

Step 2A

The end compound V is prepared by substituting a leaving group LG, for example halogen, SCN or methoxy, preferably chlorine, in a heteroaromatic system III by a nucleophile IV.

Diagram 2A

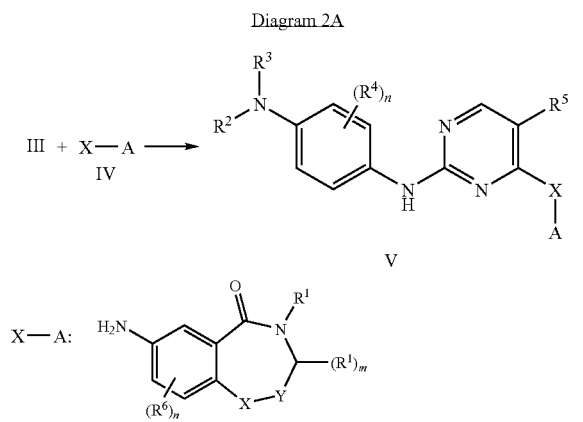

1 equivalent of the compound III and 1 to 3 equivalents of the compound IV are stirred in a solvent, for example 1,4-dioxane, N,N-dimethylformamide, N,N-dimethylacetamide or N-methyl-2-pyrrolidinone. At a temperature of 15 to 40° C., 1 to 2 equivalents of an inorganic acid, for example sulphuric acid or hydrochloric acid, are added. The reaction mixture is stirred for 12 to 72 h at a temperature of 20 to 100° C. Then the solvent is distilled off and the residue is purified by chromatography.

Method B

Step 1B

The intermediate compound VI is prepared by substitution of a leaving group LG, for example halogen, SCN or methoxy, preferably chlorine, in a heteroaromatic system I by a nucleophile IV.

Diagram 1B

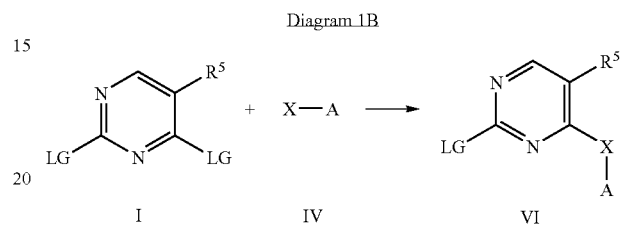

1 equivalent of compound I and 1 to 3 equivalents of a base, for example triethylamine or ethyldiisopropylamine, are stirred in a solvent, for example 1,4-dioxane, tetrahydrofuran, N,N-dimethylformamide or N,N-dimethylacetamide. At a temperature of −60 to 0° C., 0.8 to 1.5 equivalents of a compound IV are added. The reaction mixture is stirred for another 12 to 72 h at a temperature of 15 to 25° C. Then the solvent is distilled off and the residue is purified by chromatography.

Step 2B

The end compound V is prepared by substitution of a leaving group LG, for example halogen, SCN or methoxy, preferably chlorine, in a heteroaromatic system VI by a nucleophile II.

Diagram 2B

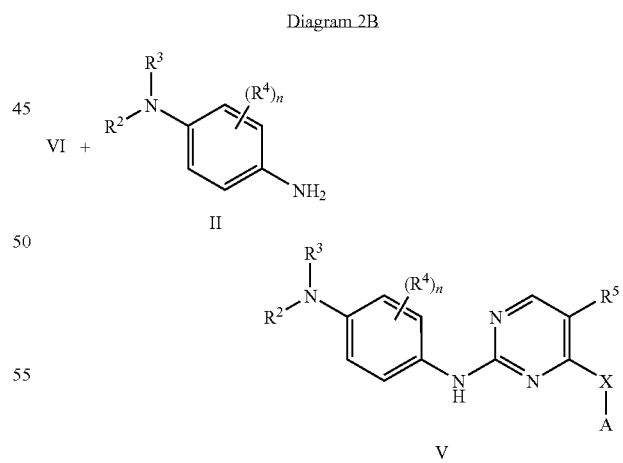

1 equivalent of compound VI and 1 to 1:5 equivalents of compound II are stirred in a solvent, for example 1,4-dioxane, N,N-dimethylformamide, N,N-dimethylacetamide or N-methyl-2-pyrrolidinone. At a temperature of 15 to 40° C., 1 to 2 equivalents of an acid, for example sulphuric acid or hydrochloric acid, are added. The reaction mixture is stirred for another 12 to 72 h at a temperature of 20 to 100° C. Then the solvent is distilled off and the residue is purified by chromatography.

Method 1

(S)-6-amino-3-ethyl-3,4-dihydro-2H-benzo[f][1,4]
oxazepin-5-one

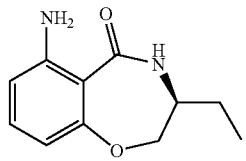

a) 2-amino-6-(2-(S)-aminobutoxy)-benzonitrile 5.01 g (51.3 mmol) (S)-2-amino-1-butanol are dissolved in 30 mL 1,4-dioxane, combined with 2.10 g (52.5 mmol) sodium hydride and stirred for 30 min at ambient temperature. To this reaction mixture are added 5.00 g (36.7 mmol) 2-amino-6-fluorobenzonitrile and the mixture is stirred for 24 h at 50° C. Then the solvent is eliminated in vacuo and the crude product is purified by chromatography. The carrier material used is silica gel and the eluant is dichloromethane to which 5% of a mixture of 90% methanol and 10% saturated aqueous ammonia solution have been added.

Yield: 5.55 g
MS (ESI): 206 (M+H)⁺ b) 2-amino-6-(2-(S)-aminobutoxy)-benzoic acid 5.53 g (27.05 mmol) (S)-2-amino-6-(1-aminomethyl-propoxy)-benzonitrile are dissolved in 70 mL of 20% ethanolic KOH and stirred for 5 d at 100° C. Then the solvent is eliminated in vacuo and the crude product is purified by chromatography. The carrier material used is silica gel and the eluant is dichloromethane to which 12% of a mixture of 90% methanol and 10% saturated aqueous ammonia solution have been added.

Yield: 4.76 g
MS (ESI): 225 (M+H)⁺ c) (S)-6-amino-3-ethyl-3,4-dihydro-2H-benzo[f][1,4]
oxazepin-5-one 4.76 g (21.23 mmol) of (S)-2-amino-6-(1-aminomethyl-propoxy)-benzoic acid are dissolved in 600 mL of tetrahydrofuran, combined with 12.5 g (63.7 mmol) 1-(3-dimethylaminopropyl)-3-ethylcarbodiimide hydrochloride and 11.11 ml (63.7 mmol) diisopropyl-ethylamine and stirred for 3 h at 50° C. Then the solvent is eliminated in vacuo and the crude product is purified by chromatography. The carrier material used is silica gel and the eluant is dichloromethane to which 4% of a mixture of 90% methanol and 10% saturated aqueous ammonia solution have been added.

Yield: 1.839 g
MS (ESI): 207 (M+H)⁺

The following compounds are prepared analogously to this method. Here, (S)-1-amino-2-butanol is replaced by a corresponding aminoalcohol.

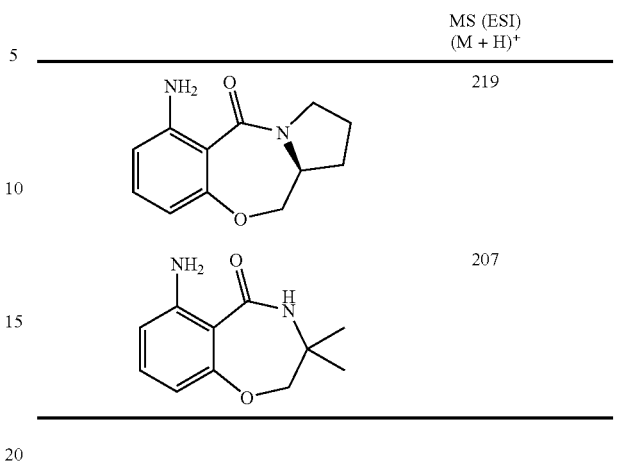

| | MS (ESI) (M + H)⁺ |
|---|---|
| | 219 |
| | 207 |

Method 2

(R)-6-amino-11a-methyl-1,2,3,11a-tetrahydro-10H-
benzo[e]pyrrolo[1,2-a][1,4]diazepine-5,11-dione

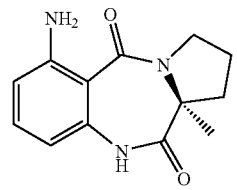

a) methyl(R)-1-(2-amino-6-nitro-benzoyl)-2-methyl-
pyrrolidine-2-carboxylate 1.18 g (6.5 mmol) 2-amino-6-nitrobenzoic acid, 0.83 g (4.6 mmol) (R)-2-methyl-pyrrolidine-2-methylester hydrochloride, 4.05 mL (23.2 mmol) N-ethyldiisopropylamine are combined with 2.5 ml of tetrahydrofuran. To this reaction mixture are added 1.71 g (5.1 mmol) O-(benzotriazol-1-yl)-N,N,N',N'-tetramethyluronium-tetrafluoroborate and the mixture is heated to 50° C. for 12 h. Then the solvent is eliminated in vacuo and the crude product is purified by chromatography. The carrier material used is silica gel and the eluant used is a mixture consisting of cyclohexane:ethyl acetate (50:50).

Yield: 930 mg
MS (ESI): 308 (M+H)⁺ b) (R)-1-(2-amino-6-nitro-benzoyl)-2-methyl-pyrro-
lidine-2-carboxylic acid 930 mg (3.02 mmol) methyl(R)-1-(2-amino-6-nitro-benzoyl)-2-methyl-pyrrolidine-2-carboxylate are dissolved in 3 mL 20% ethanolic KOH and stirred for 1.5 h at 50° C. Then the solvent is eliminated in vacuo and the crude product is purified by chromatography. The carrier material used is silica gel and the eluant used is dichloromethane, to which 15% of a mixture of 90% methanol and 10% saturated aqueous ammonia solution has been added.

Yield: 557 mg
MS (ESI): 294 (M+H)⁺ c) (R)-1-(2,6-diamino-benzoyl)-2-methyl-pyrrolidine-2-carboxylic acid 366 mg (1.25 mmol) (R)-1-(2-amino-6-nitro-benzoyl)-2-methyl-pyrrolidine-2-carboxylic acid are dissolved in 50 mL methanol and combined with 40 mg palladium on charcoal (10% Pd). The reaction mixture is hydrogenated for 9 h at 5 bar hydrogen pressure and at 25° C. Then the catalyst is filtered off, the solvent is eliminated in vacuo and the crude product is purified by chromatography. The carrier material used is C18-RP-silica gel and a gradient is run through which consists of 95% water and 5% acetonitrile at the starting point and 5% water and 95% acetonitrile at the end point.

Yield: 76 mg

MS (ESI): 264 (M+H)$^+$ d) (R)-6-amino-11a-methyl-1,2,3,11a-tetrahydro-10H-benzo[e]pyrrolo[1,2-a][1,4]diazepine-5,11-dione 76 mg (0.29 mmol) 2(R)-1-(2,6-diamino-benzoyl)-2-methyl-pyrrolidine-2-carboxylic acid are dissolved in 2 mL tetrahydrofuran, combined with 143 mg (0.9 mmol) 1-(3-dimethylaminopropyl)-3-ethylcarbodiimide hydrochloride and 103 μL (0.6 mmol) diisopropyl-ethylamine and stirred for 17 h at 50° C. Then the solvent is eliminated in vacuo and the crude product is purified by chromatography. The carrier material used is silica gel and the eluant used is dichloromethane, to which 5% of a mixture of 90% methanol and 10% saturated aqueous ammonia solution have been added.

Yield: 20 mg

MS (ESI): 246 (M+H)$^+$

The following compounds are prepared analogously:

| | MS (ESI) (M + H)$^+$: |
|---|---|
| 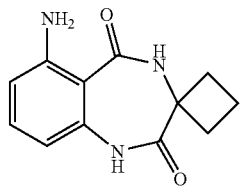 | 232 |
| 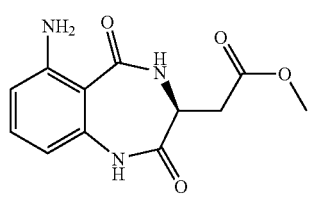 | 264 |

Method 3

Benzyl 4-(4-amino-phenyl)-piperazine-1-carboxylate

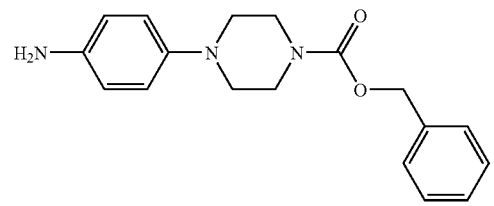

a) benzyl 4-(4-nitro-phenyl)-piperazine-1-carboxylate 3.76 ml (35.082 mmol) of 4-fluoronitrobenzene are dissolved in 40 mL DMA and combined with 9.25 mL (52.62 mmol) of N-ethyldiisopropylamine and 7.6 ml (38.59 mmol) of 1-(benzyloxycarbonyl)-piperazine. The reaction mixture is stirred for 18 h at 80° C. Then the solvent is eliminated in vacuo and the crude product is purified by chromatography. The carrier material used is silica gel and the eluant used is a mixture consisting of cyclohexane:ethyl acetate (50:50).

Yield: 11.28 g

MS (ESI): 342 (M+H)$^+$ b) benzyl 4-(4-amino-phenyl)-piperazine-1-carboxylate 11.28 g (33.04 mmol) benzyl 4-(4-nitro-phenyl)-piperazine-1-carboxylate are dissolved in 500 mL methanol and combined with 1 g Raney nickel. The mixture is hydrogenated for 18 h at 5 bar hydrogen pressure. Then the catalyst is filtered off and the residue is combined with 70 mL of aqueous 1 N hydrochloric acid and the solvent is eliminated in vacuo.

Yield: 10.89 g

MS (ESI): 312 (M+H)$^+$

The following compounds are prepared analogously to this method:

| | MS (ESI) (M + H)$^+$ |
|---|---|
| 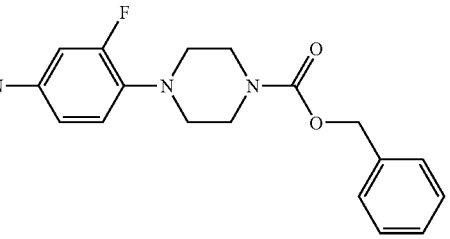 | 330 |

-continued

| | MS (ESI) (M + H)+ |
|---|---|
| 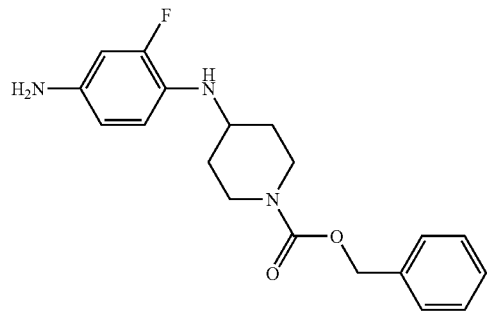 | 344 |
| | 348 |
| | 358 |
| | 362 |

-continued

| | MS (ESI) (M + H)+ |
|---|---|
| 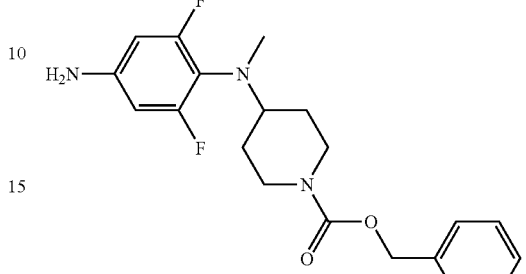 | 376 |

Chromatography

For medium pressure chromatography (MPLC) silica gel made by Millipore (name: Granula Silica Si-60A 35-70 μm) or C-18 RP-silica gel made by Macherey Nagel (name: Polygoprep 100-50 C18) is used.

For preparative high pressure chromatography columns made by Waters are used (name: XTerra Prep. MS C18, 5 μM, 30*100 mm or Symmetry C18, 5 μm, 19*100 mm)

Nuclear Magnetic Resonance (NMR) Spectroscopy

The measurements is carried out in deuterated dimethyl-sulphoxide-d6. If other solvents are used, these are explicitly mentioned in the Examples or in the methods. The measurements are recorded on a delta scale in units of ppm. Tetramethylsilane is used as the standard. The measurements are obtained using an Avance 400 (400 MHz-NMR-spectrometer) made by Bruker Biospin GmbH.

Mass Spectroscopy/UV-Spectrometry

These data are generated using an HPLC-MS apparatus (high performance liquid chromatography with mass detector) made by Agilent. The apparatus is constructed so that a diode array detector (G1315B made by Agilent) and a mass detector (1100 LS-MSD SL; G1946D; Agilent) are connected in series downstream of the chromatography apparatus (column: Zorbax SB-C8, 3.5 μm, 2.1*50, Agilent).

The apparatus is operated with a flow of 1.2 ml/min. For a separation process a gradient is run through within 3.5 min (start of gradient: 95% water and 5% acetonitrile; end of gradient: 5% water and 95% acetonitrile; in each case 0.1% formic acid is added to the two solvents).

EXAMPLE 1

2-(4-piperazin-1-yl-phenylamino)-4-((S)-4-oxo-2,3,10,10a-tetrahydro-1H.4H-9-oxa-3a-aza-benzo[f]azulen-5-ylamino)-5-trifluoromethyl-pyrimidine

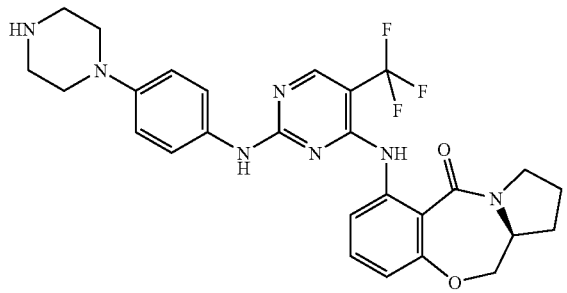

12.64 g (32.89 mmol) benzyl 4-(4-amino-phenyl)-piperazine-1-carboxylate (Method 3) are suspended in 10 mL dioxane combined with 28 mL (164.4 mmol) Hünig base and cooled to 0° C. 5 g (23 mmol) 2,4-dichloro-5-trifluoropyrimidine are slowly added. After stirring for 16 h at ambient temperature, the reaction mixture is diluted with 200 mL dichloromethane and 200 mL sodium chloride solution. The organic phase is separated off and the solvent is eliminated in vacuo. The crude product thus obtained consists of the two regioisomers. These are separated by column chromatography. The carrier material used is C18-RP-silica gel and a gradient is run through which at the starting point consists of 95% water and 5% acetonitrile and at the end point consists of 5% water and 95% acetonitrile. 0.2% Formic acid is added to the two eluants. The fractions which contain 2-(4-piperazin-1-yl-phenylamino)-4-chloro-5-trifluoromethyl-pyrimidine are freeze-dried.

400 mg (0.813 mmol) of the intermediate product thus obtained and 185 mg (0.895 mmol) (S)-5-amino-2,3,10,10a-tetrahydro-1H-9-oxa-3a-aza-benzo[f]azulen-4-one (Method 1) are dissolved in 0.5 ml N-methyl-2-pyrrolidinone and combined with 100 µL of a 4 M solution of HCl (0.406 mmol) in 1,4-dioxane. This mixture is stirred for 1.5 h at 100° C. Then 30 mL of a 1 N aqueous hydrochloric acid are added and the precipitate is removed by suction filtering. This is dried and combined with 20 mL DMF and 1 mL water dissolved with 50 mg palladium on charcoal and 50 mg palladium hydroxide and hydrogenated for 3 h at 7 bar hydrogen pressure. Then the catalyst is filtered off and the solvent is eliminated in vacuo. The crude product is purified by column chromatography. The carrier material used is C18-RP-silica gel and a gradient is run through which at the starting point consists of 95% water and 5% acetonitrile and at the end point consists of 45% water and 55% acetonitrile. 0.2% Formic acid is added to the two eluants.

Yield: 167 mg
UV max: 282 nM
MS (ESI): 540 (M+H)

$^1$H-NMR: 1.57-1.70 (m, 1H), 1.82-2.06 (m, 3H), 3.17-3.37 (m, 8H), 3.37-3.53 (m, 2H), 6.87-6.99 (m, 3H), 7.37-7.55 (m, 3H), 7.97-8.25 (m, 1H), 8.40 (s, 1H), 9.04-9.27 (m, 2H), 9.60-9.99 (m, 1H), 10.30-10.47 (m, 1H)

EXAMPLE 2

2-(4-(4-methyl-piperazin-1-yl)-phenylamino)-4-((S)-4-oxo-2,3,10,10a-tetrahydro-1H,4H-9-oxa-3a-aza-benzo[f]azulen-5-ylamino)-5-trifluoromethyl-pyrimidine

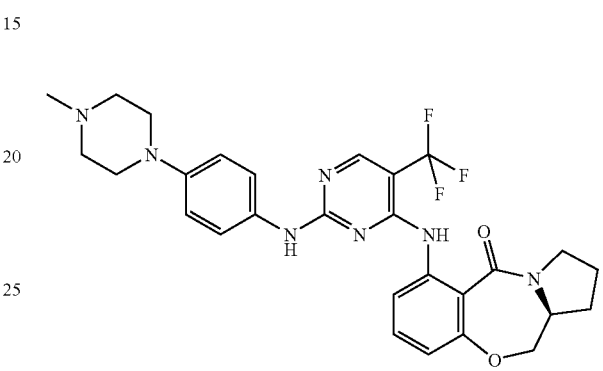

50 mg (0.077 mmol) 2-(4-piperazin-1-yl-phenylamino)-4-((S)-4-oxo-2,3,10,10a-tetrahydro-1H.4H-9-oxa-3a-aza-benzo[f]azulen-5-ylamino)-5-trifluoromethyl-pyrimidine are dissolved in 0.5 mL dimethylformamide and combined with 12 µL (0.154 mmol) formaldehyde and 2 µL (0.039 mmol) acetic acid. 86 mg (0.385 mmol) of sodium triacetoxyborohydride are metered into this mixture and it is stirred for 16 h at ambient temperature. Then the solvent is eliminated in vacuo. The crude product is purified by column chromatography. The carrier material used is C18-RP-silica gel and a gradient is run through which at the starting point consists of 95% water and 5% acetonitrile and at the end point consists of 5% water and 95% acetonitrile. 0.2% Formic acid is added to the two eluants. The suitable fractions are combined with 1 N aqueous hydrochloric acid and freeze-dried.

Yield: 49 mg
UV max: 278 nM
MS (ESI): 554 (M+H)

$^1$H-NMR: 1.58-1.72 (m, 1H), 1.84-2.10 (m, 3H), 2.87 (s, 3H), 2.95-3.08 (m, 2H), 3.12-3.26 (m, 2H), 3.38-3.48 (m, 1H), 3.49-3.59 (m, 2H), 3.63-3.73 (m, 1H), 3.75-3.89(m, 3H), 4.07-4.24 (m, 2H), 6.91-7.05 (m, 3H), 7.36-7.52 (m, 3H), 7.90-8.20 (s, 1H), 8.37-8.60 (s, 1H), 10.05-10.90 (m, 2H)

EXAMPLES 3-27

The following compounds may be prepared using an analogous method as described in Example 1. The corresponding anilines are described in Methods 1, 2 or 3 or may be obtained commercially.

| # | A | R$_x$ | UV max [nm] | MS (ESI) (M + H)$^+$ |
|---|---|---|---|---|
| 3 | (benzodiazepinedione with methyl, X$_1$) | (fluorophenyl piperazine, X$_2$) | 246, 248 | 585 |
| 4 | (benzoxazepinone, X$_1$) | (fluorophenyl piperazine, X$_2$) | 286 | 558 |
| 5 | (benzoxazepinone with ethyl, X$_1$) | (fluorophenyl piperazine, X$_2$) | 282 | 546 |
| 6 | (benzodiazepinedione with methyl, X$_1$) | (difluorophenyl piperazine, X$_2$) | 246, 286 | 603 |

-continued
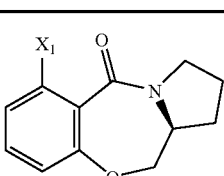
| # | A | $R_x$ | UV max [nm] | MS (ESI) $(M + H)^+$ |
|---|---|---|---|---|
| 7 | 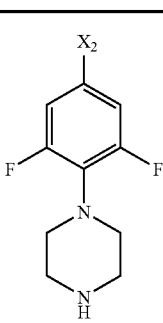 | 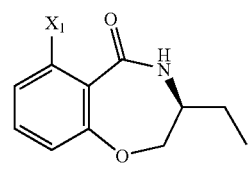 | 282 | 576 |
| 8 | 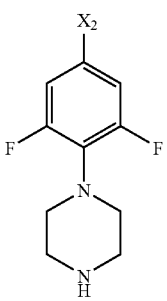 | 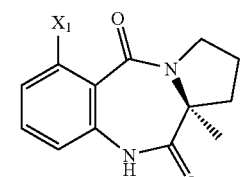 | 282 | 564 |
| 9 | 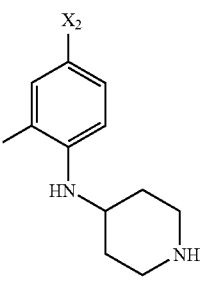 | 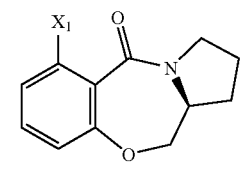 | 246, 290 | 599 |
| 10 | 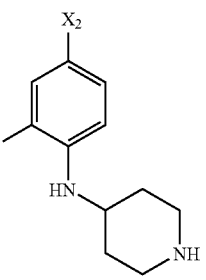 | | 286 | 572 |

-continued
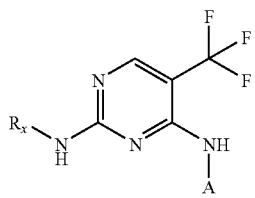
| # | A | $R_x$ | UV max [nm] | MS (ESI) $(M+H)^+$ |
|---|---|---|---|---|
| 11 | | | 286, 306 | 560 |
| 12 | | | 246, 286 | 617 |
| 13 | | | 286 | 590 |
| 14 | | | 286 | 578 |

-continued
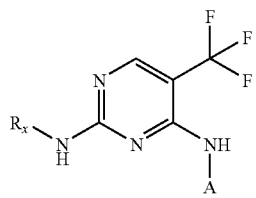
| # | A | R$_x$ | UV max [nm] | MS (ESI) (M + H)$^+$ |
|---|---|---|---|---|
| 15 | | | 246, 286 | 613 |
| 16 | | | 282 | 586 |
| 17 | | | 282 | 574 |
| 18 | | | 246, 286 | 631 |

-continued
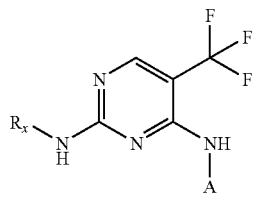
| # | A | $R_x$ | UV max [nm] | MS (ESI) $(M+H)^+$ |
|---|---|---|---|---|
| 19 | 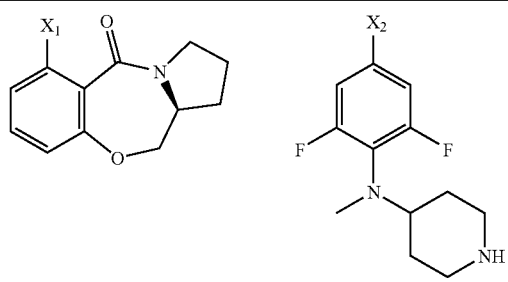 | | 282 | 604 |
| 20 | 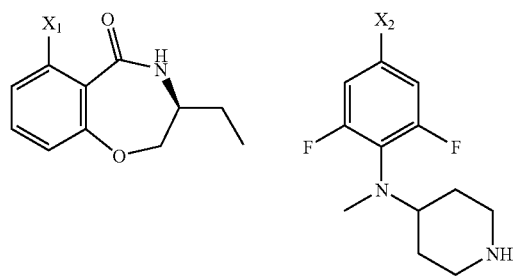 | | 282 | 592 |
| 21 | 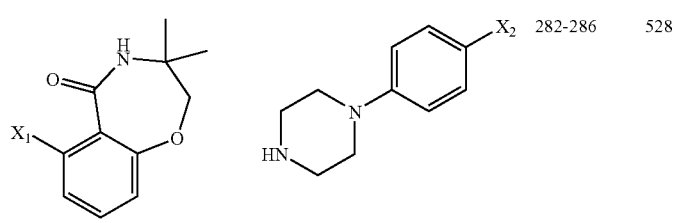 | | 282-286 | 528 |
| 22 | 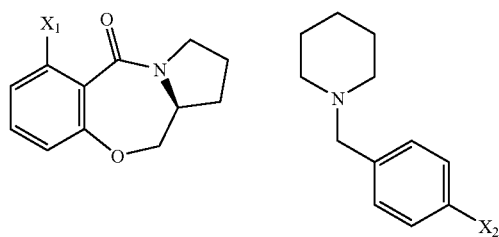 | | 278 | 553 |

-continued
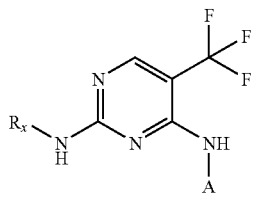
| # | A | Rx | UV max [nm] | MS (ESI) (M + H)+ |
|---|---|----|-------------|-------------------|
| 23 | (X1-substituted benzoxazepinone with gem-dimethyl) | (piperidinylmethyl-phenyl-X2) | 278-282 | 541 |
| 24 | (X1-substituted benzoxazepinone with ethyl) | (piperazinyl-phenyl-X2) | 282 | 528 |
| 25 | (X1-substituted pyrrolidine-fused benzoxazepinone) | (piperazinyl-phenyl-X2) | 282 | 540 |
| 26 | (X1-substituted benzodiazepinedione with cyclobutyl) | (piperazinyl-phenyl-X2) | 250, 286 | 554 |

-continued

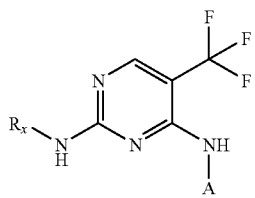

| # | A | $R_x$ | UV max [nm] | MS (ESI) $(M + H)^+$ |
|---|---|---|---|---|
| 27 | ![A structure with X₁] | ![Rx structure with X₂] | 246, 286 | 585 |

EXAMPLES 28-81

The following compounds may be obtained by an analogous method to that described in Example 2. The corresponding starting material is prepared by an analogous method to that described in Example 1.

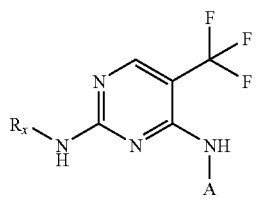

| # | A | $R_x$ | UV max [nm] | MS (ESI) $(M + H)^+$ |
|---|---|---|---|---|
| 28 | ![A structure with X₁] | ![Rx structure with X₂, N-methyl piperidine] | 254, 286 | 595 |
| 29 | ![A structure with X₁] | ![Rx structure with X₂, N-ethyl piperidine] | 250, 286 | 609 |

-continued

| # | A | $R_x$ | UV max [nm] | MS (ESI) $(M + H)^+$ |
|---|---|---|---|---|
| 30 | | | 246, 290 | 643 |
| 31 | | | 250, 282 | 568 |
| 32 | | | 282 | 582 |
| 33 | | | 280, 302 | 608 |

-continued
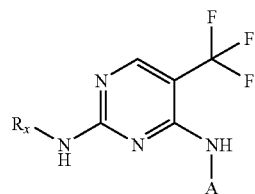
| # | A | Rx | UV max [nm] | MS (ESI) (M + H)+ |
|---|---|----|----|----|
| 34 | | | 283 | 556 |
| 35 | | | 250, 280 | 570 |
| 36 | | | 242, 285, 306 | 596 |
| 37 | | | 246, 286 | 599 |

-continued

| # | A | R$_x$ | UV max [nm] | MS (ESI) (M + H)$^+$ |
|---|---|---|---|---|
| 38 | | | 282 | 572 |
| 39 | | | 282 | 560 |
| 40 | | | 246, 286 | 616 |
| 41 | | | 282 | 590 |

-continued
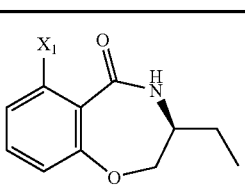
| # | A | $R_x$ | UV max [nm] | MS (ESI) $(M + H)^+$ |
|---|---|---|---|---|
| 42 | 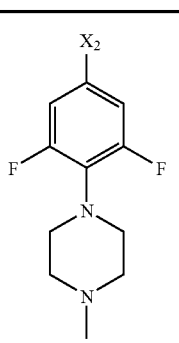 | 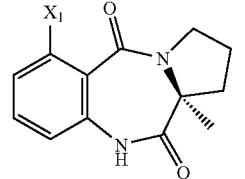 | 282 | 578 |
| 43 | 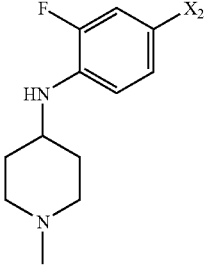 | 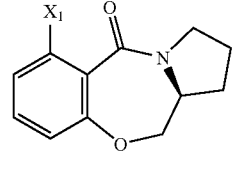 | 246, 286 | 613 |
| 44 | 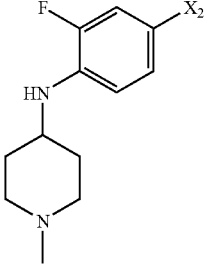 | 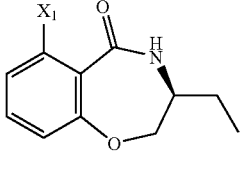 | 282 | 586 |
| 45 | 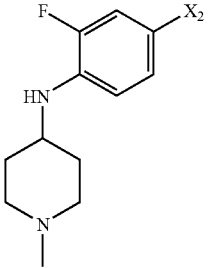 | 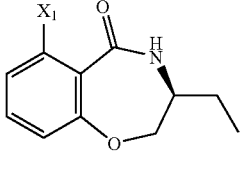 | 282 | 574 |

-continued
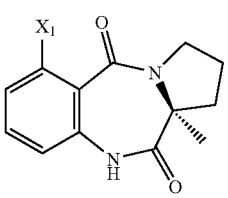
| # | A | R$_x$ | UV max [nm] | MS (ESI) (M + H)$^+$ |
|---|---|---|---|---|
| 46 | 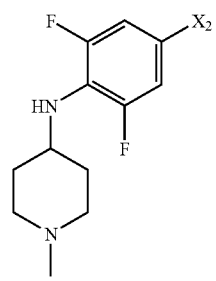 | 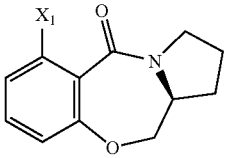 | 246, 286 | 631 |
| 47 | 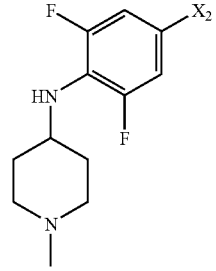 | 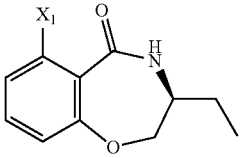 | 282 | 604 |
| 48 | 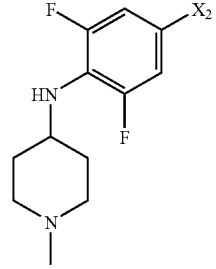 | 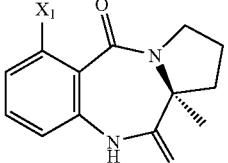 | 282 | 592 |
| 49 | 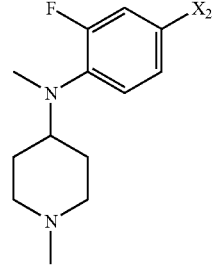 |  | 246, 286 | 627 |

-continued
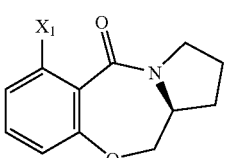
| # | A | Rx | UV max [nm] | MS (ESI) (M + H)+ |
|---|---|---|---|---|
| 50 | 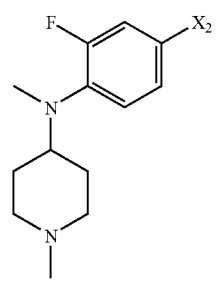 | 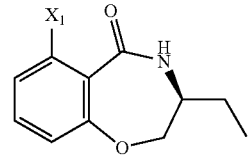 | 282 | 600 |
| 51 | 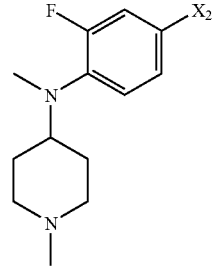 | 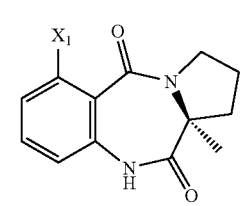 | 282 | 588 |
| 52 | 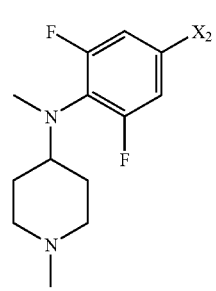 | 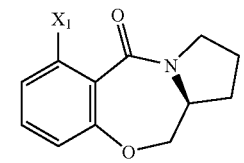 | 246, 286 | 645 |
| 53 | 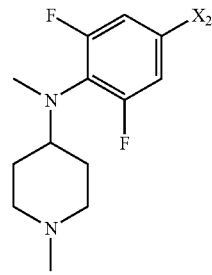 | | 282 | 618 |

-continued
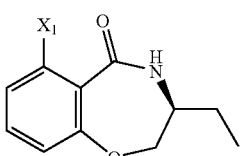
| # | A | Rx | UV max [nm] | MS (ESI) (M + H)+ |
|---|---|---|---|---|
| 54 | 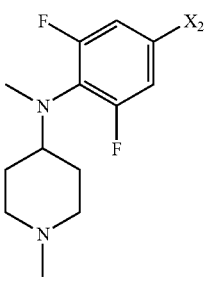 | 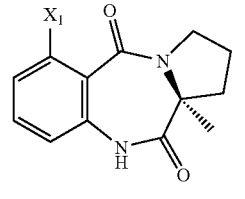 | 282 | 606 |
| 55 | 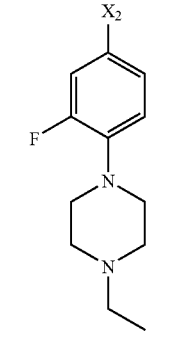 | 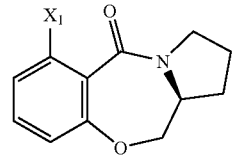 | 246, 286 | 613 |
| 56 | 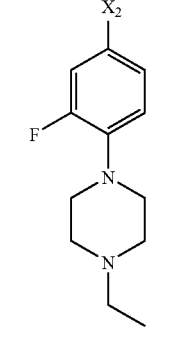 | 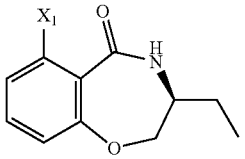 | 282 | 586 |
| 57 | 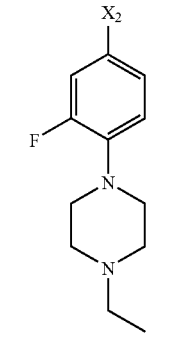 | | 282 | 574 |

-continued
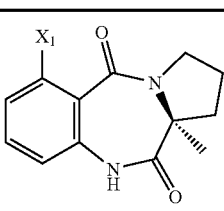
| # | A | $R_x$ | UV max [nm] | MS (ESI) (M + H)⁺ |
|---|---|---|---|---|
| 58 | 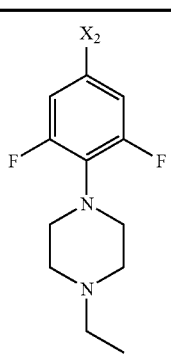 | 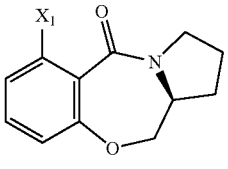 | 246, 286 | 631 |
| 59 | 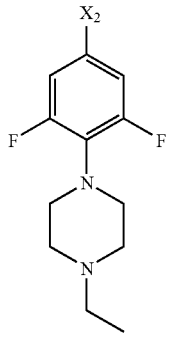 | 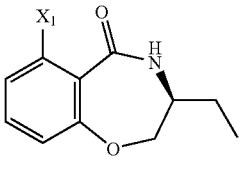 | 282 | 604 |
| 60 | 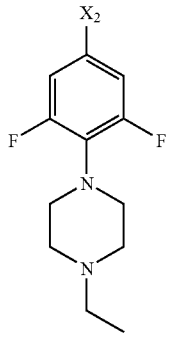 | 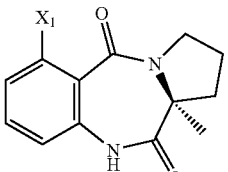 | 282 | 592 |
| 61 | 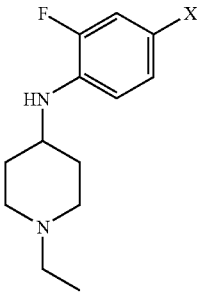 | | 246, 286 | 627 |

-continued
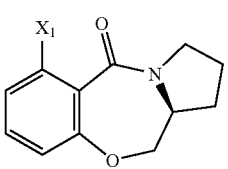
| # | A | $R_x$ | UV max [nm] | MS (ESI) $(M + H)^+$ |
|---|---|---|---|---|
| 62 | 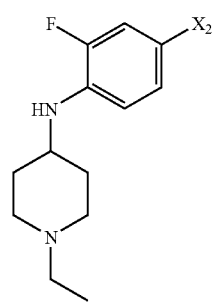 | 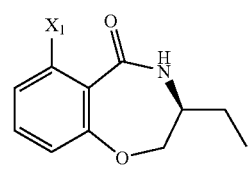 | 282 | 600 |
| 63 | 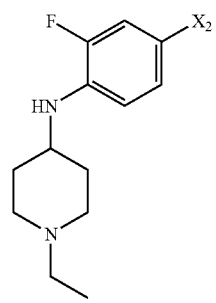 | 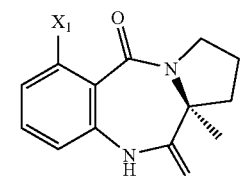 | 282 | 588 |
| 64 | 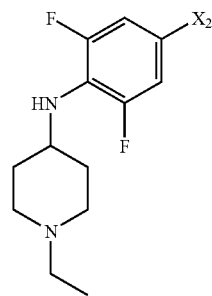 | 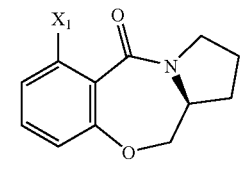 | 246, 286 | 645 |
| 65 | 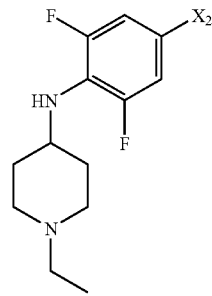 | | 282 | 618 |

-continued
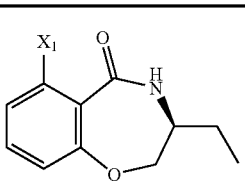
| # | A | $R_x$ | UV max [nm] | MS (ESI) $(M + H)^+$ |
|---|---|---|---|---|
| 66 | 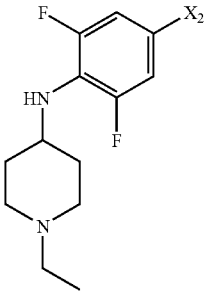 | 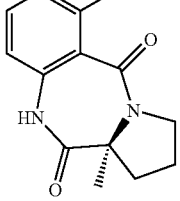 | 282 | 606 |
| 67 | 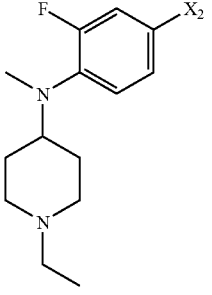 | 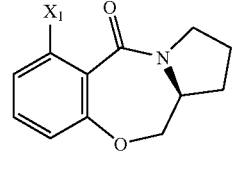 | 246, 286 | 641 |
| 68 | 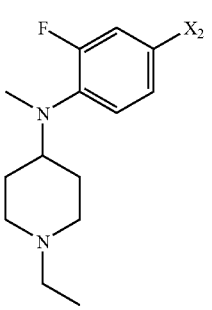 | 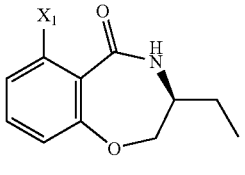 | 282 | 614 |
| 69 | 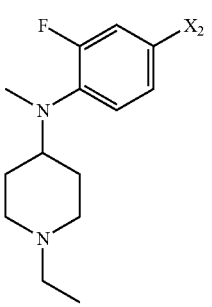 | 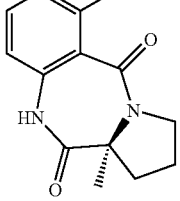 | 282 | 602 |

-continued

| # | A | $R_x$ | UV max [nm] | MS (ESI) $(M+H)^+$ |
|---|---|---|---|---|
| 70 | (structure) | (structure) | 246, 286 | 659 |
| 71 | (structure) | (structure) | 282 | 632 |
| 72 | (structure) | (structure) | 282 | 620 |
| 73 | (structure) | (structure) | 246, 282 | 581 |

-continued
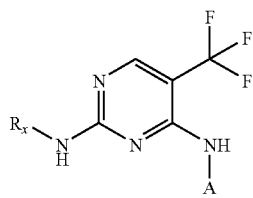
| # | A | $R_x$ | UV max [nm] | MS (ESI) $(M + H)^+$ |
|---|---|---|---|---|
| 74 | | | 282-286 | 642 |
| 75 | | | 282 | 570 |
| 76 | | | 282-286 | 582 |
| 77 | | | 282 | 542 |
| 78 | | | 282 | 556 |
| 79 | | | 282 | 582 |

-continued

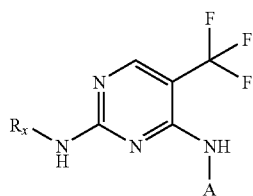

| # | A | R$_x$ | UV max [nm] | MS (ESI) (M + H)$^+$ |
|---|---|---|---|---|
| 80 | (benzodiazepinedione with cyclobutyl, X$_1$) | ethylpiperazinyl-phenyl-X$_2$ | 250, 286 | 581 |
| 81 | (benzodiazepinedione with CH$_2$CO$_2$Me, X$_1$) | ethylpiperazinyl-phenyl-X$_2$ | 248, 286 | 613 |

EXAMPLES 82-91

The following compounds may be obtained by an analogous method to that described in Example 2. The corresponding starting material is prepared by an analogous method to that described in Example 1.

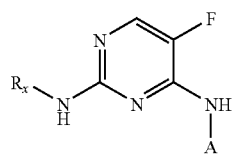

| # | A | R$_x$ | UV max [nm] | MS (ESI) (M + H)$^+$ |
|---|---|---|---|---|
| 82 | (benzoxazepinone with ethyl, X$_1$) | methylpiperazinyl-piperidinyl-phenyl-X$_2$ | 318 | 575 |

-continued

| # | A | R$_x$ | UV max [nm] | MS (ESI) (M + H)$^+$ |
|---|---|---|---|---|
| 83 | | | 250-254 | 614 |
| 84 | | | 240/284 | 559 |
| 85 | | | 238/282/338 | 531 |
| 86 | | | 274 | 552 |
| 87 | | | 274 | 564 |

-continued
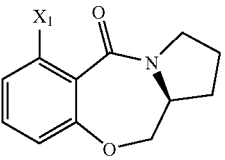
| # | A | Rx | UV max [nm] | MS (ESI) (M + H)+ |
|---|---|----|-------------|-------------------|
| 88 | 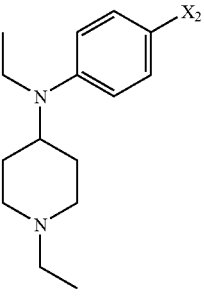 | 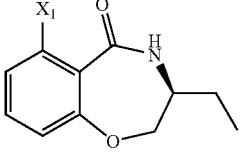 | 282 | 560 |
| 89 | 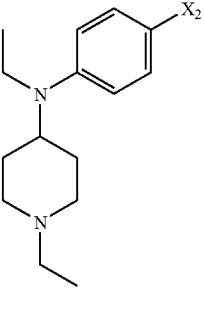 | 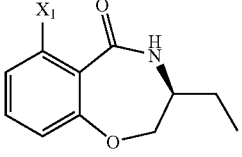 | 282 | 548 |
| 90 | 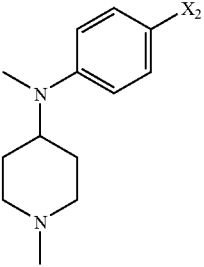 | 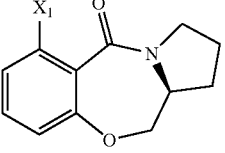 | 282 | 520 |
| 91 | 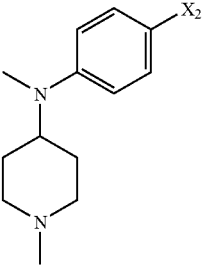 | | 282 | 532 |

The following Examples describe the biological activity of the compounds according to the invention without restricting the invention to these Examples.

The activity of the compounds according to the invention on various kinases, for example on serine-threonine kinase PLK-1, was determined by in vitro kinase assays with recombinantly produced protein. In this assay the compounds exhibit a good to very good effect on PLK1, i.e. for example an IC50 value of less than 1 μmol/L, usually less than 0.1 μmol/L.

Example PLK-1 Kinase Assay

Recombinant human PLK1 enzyme linked to GST at its N-terminal end is isolated from insect cells infected with baculovirus (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 μM) and the suspension is incubated further. The cell number is determined, the cells are removed by centrifuging (5 minutes, 4° C., 800 rpm) and washed 1× with PBS (8 g NaCl/l, 0.2 g KCl/l, 1.44 g $Na_2HPO_4$/l, 0.24 g $KH_2PO4$/l). After centrifuging again the pellet is flash-frozen in liquid nitrogen. Then the pellet is quickly thawed and resuspended in ice-cold lysing buffer (50 mM HEPES pH 7.5, 10 mM $MgCl_2$, 1 mM DTT, 5 μg/ml leupeptin, 5 μg/ml aprotinin, 100 μM NaF, 100 μM PMSF, 10 mM β-glycerol phosphate, 0.1 mM $Na_3VO_4$, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysing buffer and the recombinant protein is eluted from the beads with 1 ml eluting buffer/ml resuspended beads (eluting buffer: 100 mM Tris/HCl pH=8.0, 120 mM NaCl, 20 mM reduced glutathione (Sigma G-4251), 10 mM $MgCl_2$, 1 mM DTT). The protein concentration is determined by Bradford Assay.

Kinase Assay

The following components are combined in a well of a 96-well round-bottomed dish (Greiner bio-one, PS Microtitre plate No. 650101):

10 μl of the compound to be tested in variable concentrations (e.g. beginning at 300 μM, and dilution to 1:3) in 6% DMSO, 0.5 mg/ml casein (Sigma C-5890), 60 mM β-glycerophosphate, 25 mM MOPS pH=7.0, 5 mM EGTA, 15 mM $MgCl_2$, 1 mM DTT 20 μl substrate solution (25 mM MOPS pH=7.0, 15 mM $MgCl_2$, 1 mM DTT, 2.5 mM EGTA, 30 mM β-glycerophosphate, 0.25 mg/ml casein)

20 μl enzyme dilution (1:100 dilution of the enzyme stock in 25 mM MOPS pH=7.0, 15 mM $MgCl_2$, 1 mM DTT)

10 μl ATP solution (45 μM ATP with $1.11 \times 10^6$ Bq/ml gamma-P33-ATP).

The reaction is started by adding the ATP solution and continued for 45 minutes at 30° C. with gentle shaking (650 rpm on an IKA MTS2 shaker). The reaction is stopped by the addition of 125 μl of ice-cold 5% TCA per well and incubated on ice for at least 30 minutes. The precipitate is transferred by harvesting onto filter plates (96-well microtitre filter plate: UniFilter-96, GF/B; Packard; No. 6005177), then washed four times with 1% TCA and dried at 60° C. After the addition of 35 μl scintillation solution (Ready-Safe; Beckmann) per well the plate is sealed shut with sealing tape and the amount of P33 precipitated is measured with the Wallac Betacounter. The measured data are evaluated using the standard Graphpad software (Levenburg-Marquard algorithm).

Example Aurora-B Kinase Assay

A radioactive enzyme inhibition assay was developed using Baculovirus-expressed recombinant human Aurora B wild-type protein equipped at the N-terminal position with a histidine (6) epitope (His-), which is obtained from infected insect cells (SF21) and purified.

Expression and Purification

For this, $300 \times 10^6$ SF21 cells in SF-900II insect cell medium (Invitrogen) are incubated for example with a suitable amount of Baculovirus solution for 1 h at 27° C. (Fernbach flask agitator, 50 rpm). Then 250 ml SF-900 II medium is added and agitated for 3 days (100 rpm, 27° C.). Three hours before harvesting, okadaic acid ($C_{44}H_{68}O_{13}$, Calbiochem #495604) is added (final concentration 0.1 μM) in order to stabilise phosphorylation sites on recombinant Aurora B. The cells are pelleted by centrifugation (1000 rpm, 5 min, 4° C.), the supernatant is discarded and the pellet is frozen in liquid nitrogen. The pellet is thawed (37° C., 5 min) and resuspended in lysing buffer. 40 mL lysing buffer (25 mM Tris/Cl, 10 mM $MgCl_2$, 300 mM NaCl, 20 mM imidazole, pH 8.0, 0.07% 2-mercaptoethanol and Protease-Inhibitor-Complete from Roche Diagnostics) is used for 200 mL of volume of the starting culture. After two rapid freezing/thawing cycles (liquid nitrogen at 37° C.), the lysate is kept on ice for 30 min, then incubated (2 h, 4° C.) with washed Ni-NTA beads (Ni-NTA Superflow Beads, 4 mL per 200 mL of starting culture) and placed in an Econo-Pac column (Biorad #732-1010). Five washes with in each case 10 column volumes of washing buffer (25 mM Tris/Cl, 10 mM $MgCl_2$, 1000 mM NaCl, 20 mM imidazole, pH 8.0, 0.07% 2-mercaptoethanol and Protease-Inhibitor-Complete from Roche Diagnostics) precede the elution in 8 ml (per 200 ml of starting culture) elution buffer (25 mM Tris/Cl pH 8.0, 300 mM NaCl, 10 mM MgCl2, 0.03% Brij-35, 10% glycerol, 0.07% 2-mercaptoethanol, 400 mM imidazole). The combined eluate fractions are desalinated using a Sephadex G25 column and transferred into freezing buffer (50 mM tris/Cl pH 8.0, 150 mM NaCl, 0.1 mM EDTA, 0.03% Brij-35, 10% glycerol, 1 mM DTT).

Kinase Assay

Test substances are placed in a polypropylene dish (96 wells, Greiner #655 201), in order to cover a concentration frame of 10 μM-0.0001 μM. The final concentration of DMSO in the assay is 5%. 30 μL of protein mix (50 mM tris/Cl pH 7.5, 25 mM $MgCl_2$, 25 mM NaCl, 167 μM ATP, 200 ng His-Aurora B in freezing buffer) are pipetted into the 10 μl of test substance provided in 25% DMSO and this is incubated for 15 min at RT. Then 10 μL of peptide mix (100 mM tris/Cl pH 7.5, 50 mM $MgCl_2$, 50 mM NaCl, 5 μM NaF, 5 μM DTT, 1 μCi gamma-P33-ATP [Amersham], 50 μM substrate peptide [biotin-EPLERRLSLVPDS or multimers thereof, or biotin-EPLERRLSLVPKM or multimers thereof, or biotin-LRRWSLGLRRWSLGLRRWSLGLRRWSLG]) are added. The reaction is incubated for 75 min (ambient temperature) and stopped by the addition of 180 μL of 6.4% trichloroacetic acid and incubated for 20 min on ice. A multiscreen filtration plate (Millipore, MAIP NOB10) is equilibrated first of all with 100 μL 70% ethanol and then with 180 μL trichloroacetic acid and the liquids are eliminated using a suitable suction apparatus. Then the stopped kinase reaction is applied. After 5 washing steps with 180 μL 1% trichloroacetic acid in each case the lower half of the dish is dried (10-20 min at 55° C.) and 25 µL scintillation cocktail (Microscint, Packard # 6013611) is added. Incorporated gamma-phosphate is quantified using a Wallac 1450 Microbeta Liquid Scintillation Counter. Samples without test substance or without substrate peptide are used as controls. $IC_{50}$ values are obtained using Graph Pad Prism software.

The anti-proliferative activity of the compounds according to the invention is determined in the cytotoxicity test on cultivated human tumour cells and/or in a FACS analysis, for example on HeLa S3 cells. In both test methods the compounds exhibit good to very good activity, i.e. for example an EC50 value in the HeLa S3 cytotoxicity test of less than 5 µmol/L, generally less than 1 µmol/L.

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) are cultivated in Ham's F12 Medium (Life Technologies) and 10% foetal calf serum (Life Technologies) and harvested in the log growth phase. Then the HeLa S3 cells are placed in 96-well plates (Costar) at a density of 1000 cells per well and incubated overnight in an incubator (at 37° C. and 5% $CO_2$), while on each plate 6 wells are filled with medium alone (3 wells as the medium control, 3 wells for incubation with reduced AlamarBlue reagent). The active substances are added to the cells in various concentrations (dissolved in DMSO; DMSO final concentration: 0.1%) (in each case as a triple measurement). After 72 hours incubation 20 µl AlamarBlue reagent (AccuMed International) are added to each well, and the cells are incubated for a further 5-7 hours. As a control, 20 µl reduced AlamarBlue reagent is added to each of 3 wells (AlamarBlue reagent, which is autoclaved for 30 min). After incubation the colour change of the AlamarBlue reagent in the individual wells is determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity is calculated as a percentage of the control (HeLa S3 cells without inhibitor) and the active substance concentration which inhibits the cell activity by 50% (IC50) is derived. The values are calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $1 \times 10^6$ HeLa S3 cells are seeded onto a 75 cam cell culture flask, and after 24 h either 0.1% DMSO is added as control or the substance is added in various concentrations (in 0.1% DMSO). The cells are incubated for 24 h with the substance or with DMSO before the cells are washed 2× with PBS and then detached with trypsin/EDTA. The cells are centrifuged (1000 rpm, 5 min, 4° C.), and the cell pellet is washed 2× with PBS before the cells are resuspended in 0.1 ml PBS. Then the cells are fixed with 80% ethanol for 16 hours at 4° C. or alternatively for 2 hours at −20° C. The fixed cells are centrifuged (1000 rpm, 5 min, 4° C.), washed with PBS and then centrifuged again. The cell pellet is resuspended in 2 ml 0.25% Triton X-100 in PBS, and incubated on ice for 5 min before 5 ml PBS are added and the mixture is centrifuged again. The cell pellet is resuspended in 350 µl PI staining solution (0.1 mg/ml RNase A (Sigma, No. R-4875), 10 µg/ml propidium iodide (Sigma, No. P-4864) in 1×PBS). The cells are incubated for 20 min in the dark with the staining buffer before being transferred into sample measuring containers for the FACS scan. The DNA measurement is carried out in a Becton Dickinson FACS Analyzer, with an argon laser (500 mW, emission 488 nm), and the DNA Cell Quest Programme (BD). The logarithmic PI fluorescence is determined with a band-pass filter (BP 585/42). The cell populations in the individual cell cycle phases are quantified using the ModFit LT Programme made by Becton Dickinson.

The compounds according to the invention are also tested accordingly for other tumour cells. For example, these compounds are effective on carcinomas of all kinds of tissue (e.g. breast (MCF7); colon (HCT116), head and neck (FaDu), lung (NCI-H460), pancreas (BxPC-3), prostate (DU145)), sarcomas (e.g. SK-UT-1B), leukaemias and lymphomas (e.g. HL-60; Jurkat, THP-1) and other tumours (e.g. melanomas (BRO), gliomas (U-87MG)) and could be used for such indications. This is evidence of the broad applicability of the compounds according to the invention for the treatment of all kinds of tumour types.

On the basis of their biological properties the new compounds of general formula (I), their isomers and the physiologically acceptable salts thereof are suitable for treating diseases characterised by excessive or anomalous cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example platelet derived growth factor and hepatocyte growth factor, inhibitors are for example growth factor antibodies, growth factor receptor antibodies and tyrosinekinase inhibitors, such as for example gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may also consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of pharmaceutical formulations

| A) Tablets | per tablet |
|---|---|
| active substance | 100 mg |
| lactose | 140 mg |

| A) Tablets | per tablet |
|---|---|
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claim is:

1. A compound of the formula (1)

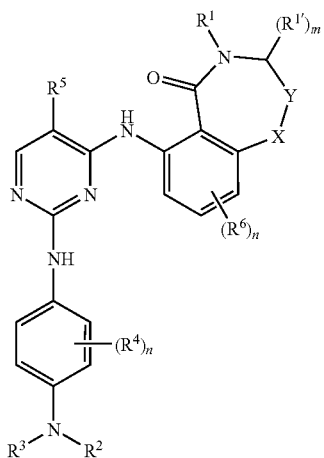

wherein

X denotes oxygen or nitrogen, and

Y denotes —$CH_2$ or C=O, and $R^1$ and $R^{1'}$ each independently of one another denote hydrogen or an optionally mono- or polysubstituted group selected from among $C_{1-5}$-alkyl, $C_{3-6}$-cycloalkyl, aryl, heterocyclyl and heteroaryl, wherein the substituent(s) may be identical or different and are selected from among halogen, —$OR^a$, —C(=O)$R^a$, —C(=O)$OR^a$, —C(=O)$NR^aR^a$, —$NR^aR^a$, —$NR^aC$(=O)$R^a$, —$NR^aC$(=O)$OR^a$, —$NR^aC$(=O)$NR^aR^a$, —$NR^aSO_2R^a$, —N=$CR^aR^a$, —$SR^a$, —$SOR^a$, —$SO_2R^a$, —$SO_2NR^aR^a$, —$NR^aSO_2NR^aR^a$, —$OSO_2NR^aR^a$ and pseudohalogen, or optionally two $R^{1'}$ groups on the same carbon atom may together with the carbon atom to which they are attached form a $C_{3-7}$ cycloalkyl ring, or optionally $R^1$ may together with an $R^{1'}$ group form a saturated or partly saturated 3-6 membered alkyl bridge, which may optionally contain one to two heteroatoms chosen from nitrogen, oxygen or sulphur, and $R^2$ denotes an optionally mono- or polysubstituted heterocyclyl group, wherein the substituent(s) may be identical or different and are selected from among $C_{1-5}$-alkyl, $C_{2-5}$-alkenyl, $C_{2-5}$-alkynyl, $C_{3-6}$-cycloalkyl-$C_{0-3}$-alkyl, and $R^3$ denotes hydrogen or $C_{1-3}$-alkyl, or $R^2$ and $R^3$ together form an optionally mono- or polysubstituted heterocyclyl ring, wherein the substituent(s) may be identical or different and are selected from among $C_{1-5}$-alkyl, $C_{2-5}$-alkenyl, $C_{2-5}$-alkynyl and $C_{3-6}$-cycloalkyl-$C_{0-3}$-alkyl, or a suitable substituent selected from among halogen, —$OR^a$, —C(=O)$R^a$, —C(=O)$OR^a$, —C(=O)$NR^aR^a$, —$NR^aR^a$, —$NR^aC$(=O)$R^a$, —$NR^aC$(=O)$OR^a$, —$NR^aC$(=O)$NR^aR^a$, —$NR^aSO_2R^a$, —N=$CR^aR^a$, —$SR^a$, —$SOR^a$, —$SO_2R^a$, —$SO_2NR^aR^a$, —$NR^aSO_2NR^aR^a$, —$OSO_2NR^aR^a$ and pseudohalogen, and $R^4$ each independently of one another denote a group selected from among halogen, $NO_2$, —$OR^a$, —C(=O)$R^a$, —C(=O)$OR^a$, —C(=O)$NR^aR^a$, —$NR^aR^a$, —$NR^aCOR^a$, —$NR^aC$(=O)$OR^a$, —$NR^aC$(=O)$NR^aR^a$, —$NR^aC$(=O)$ONR^aR^a$, —$NR^aSO_2R^a$, —N=$CR^aR^a$, —$SR^a$, —$SOR^a$, —$SO_2R^a$, —$SO_2NR^aR^a$, —$NR^aSO_2NR^aR^a$, —$OSO_2NR^aR^a$ and pseudohalogen; and $R^5$ denotes hydrogen, halogen, $C_{1-3}$-alkyl, $C_{2-3}$-alkenyl, $C_{2-3}$-alkynyl, halogen-$C_{1-3}$-alkyl, —$OR^a$ or pseudohalogen, and $R^6$ each independently of one another denote a group selected from among halogen, $C_{1-3}$-alkyl, —$OR^a$ and pseudohalogen, and $R^a$ each independently of one another denote hydrogen or a group selected from among optionally substituted $C_{1-8}$-alkyl, $C_{2-8}$-alkenyl, $C_{2-8}$-alkynyl, $C_{3-10}$-cycloalkyl, aryl, heterocyclyl and heteroaryl, while the substituent(s) may be identical or different and are selected from among halogen, —$NH_2$, —OH and pseudohalogen; and m denotes 0, 1 or 2; and n each independently of one another denote 0, 1, or 2, wherein the term heteroaryl in each instance is independently chosen from furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide;

wherein the term heterocyclyl in each instance is independently chosen from tetrahydrofuranyl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo [2.2.1]heptane, 8-oxa-3-aza-bicyclo[3.2.1]octane, 3,8-diaza-bicyclo [3.2.1]octane, 2,5-diaza-bicyclo[2.2.1]heptane, 3,8-diaza-bicyclo [3.2.1] octane, 3,9-diaza-bicyclo[4.2.1]nonane and 2,6-diazabicyclo [3.2.2]nonane;

or a tautomer, racemate, enantiomer, diastereomer or mixture thereof, or a pharmacologically acceptable salt thereof, with the proviso that 2-(2-methoxy-4-piperazin-1-yl-phenylamino)-4-(3,3-dimethyl-5-oxo-2,3,4,5-benzo [f][1,4]oxazepin-6-ylamino-5-trifluoromethyl-pyrimidine, 2-(2-methoxy-4-piperazin-1-yl-phenylamino)-4-((S)-4-oxo-2,3,10,10a-tetrahydro-1H, 4H-9-oxa-3a-aza-benzo[f]azulen-5-ylamino-5-trifluoromethyl-pyrimidine, 2-[4-(4-ethyl-piperazin-1-yl)-2-methoxy-phenylamino]-4-((S)-4-oxo-2,3,10,10a-tetrahydro-1H,4H-9-oxa-3a-aza-benzo[f]azulen-5-ylamino-5-trifluoromethyl-pyrimidine, 2-[4-(4-methyl-piperazin-1-yl)-2-methoxy-phenylamino]-4-((S)-4-oxo-2,3,10,10a-tetrahydro-1H,4H-9-oxa-3a-aza-benzo [f]azulen-5-ylamino-5-trifluoromethyl-pyrimidine, 3,3-dimethyl-6-{2-[4-(4-methyl-piperazin-1-yl)-phenylamino]-5-trifluoromethyl-pyrimidin-4-ylamino}-3,4-dihydro-2H-benzo[f][1,4]oxazepin-5-one, 6-{2-[4-(4-ethyl-piperazin-1-yl)-phenylamino]-5-trifluoromethyl-pyrimidin-4-ylamino}-3,3-dimethyl-3,4-dihydro-2H-benzo[f][1,4]oxazepin-5-one, 3,3-dimethyl-6-{2-[4-(4-prop-2-ynyl-piperazin-1-yl)-phenylamino]-5-trifluoromethyl-pyrimidin-4-ylamino}-3,4-dihydro-2H-benzo[f][1,4]oxazepin-5-one, 6-{2-[4-(4-isopropyl-piperazin-1-yl)-phenylamino]-5-trifluoromethyl-pyrimidin-4-ylamino}-3,3-dimethyl-3,4-dihydro-2H-benzo[f][1,4] oxazepin-5-one, (S)-3-methyl-6-[2-(4-piperazin-1-yl-phenylamino)-5-trifluoromethyl-pyrimidin-4-ylamino]-3,4-dihydro-2H-benzo[f][1,4]oxazepin-5-one, (S)-3-methyl-6-{2-[4-(4-methyl-piperazin-1-yl)-phenylamino]-5-trifluoromethyl-pyrimidin-4-ylamino}-3,4-dihydro-2H-benzo[f][1,4]oxazepin-5-one, (S)-6-{2-[4-(4-isopropyl-piperazin-1-yl)-phenylamino]-5-trifluoromethyl-pyrimidin-4-ylamino}-3-methyl-3,4-dihydro-2H-benzo[f][1,4] oxazepin-5-one, (S)-3-methyl-6-{2-[4-(4-prop-2-ynyl-piperazin-1-yl)-phenylamino]-5-trifluoromethyl-pyrimidin-4-ylamino}-3,4-dihydro-2H-benzo[f][1,4] oxazepin-5-one, (S)-3-ethyl-6-[2-(4-piperazin-1-yl-phenylamino)-5-trifluoromethyl-pyrimidin-4-ylamino]-3,4-dihydro-2H-benzo[f][1,4]oxazepin-5-one, (S)-6-[2-(4-piperazin-1-yl-phenylamino)-5-trifluoromethyl-pyrimidin-4-ylamino]-3-propyl-3,4-dihydro-2H-benzo[f][1,4]oxazepin-5-one, (S)-6-{2-[4-(4-prop-2-ynyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-ethyl-piperazin-1-yl)-phenylamino]-5-trifluoromethyl-pyrimidin-4-ylamino}-1,2,3,11a-tetrahydro-10H-benzo[e]pyrrolo [1,2-a][1,4]diazepine-5,11-dione, (S)-6-{2-[4-(4-isobutyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-methyl-piperazin-1-yl)-phenylamino]-5-trifluoromethyl-pyrimidin-4-ylamino}-1,2,3,11a-tetrahydro-10H-benzo[e]pyrrolo [1,2-a][1,4]diazepine-5,11-dione, 6-{2-[4-(4-ethyl-piperazin-1-yl)-phenylamino]-5-trifluoromethyl-pyrimidin-4-ylamino}-3,3-dimethyl-3,4-dihydro-1H-benzo[e][1,4]diazepine-2,5-dione, 3,3-dimethyl-6-{2-[4-(4-methyl-piperazin-1-yl)-phenylamino]-5-trifluoromethyl-pyrimidin-4-ylamino}-3,4-dihydro-1H-benzo[e][1,4]diazepine-2,5-dione, 6-{2-[4-(4-isopropyl-piperazin-1-yl)-phenylamino]-5-trifluoromethyl-pyrimidin-4-ylamino}-3,3-dimethyl-3, 4-dihydro-1H-benzo[e][1,4]diazepine-2,5-dione, 3,3-dimethyl-6-{2-[4-(4-prop-2-ynyl-piperazin-1-yl)-phenylamino]-5-trifluoromethyl-pyrimidin-4-ylamino}-3,4-dihydro-1H-benzo[e][1,4]diazepine-2,5-dione, (S)-6-{2-[4-(4-isopropyl-piperazin-1-yl)-phenylamino]-5-trifluoromethyl-pyrimidin-4-ylamino}-1,2,3,11a-tetrahydro-10H-benzo[e]pyrrolo[1,2-a][1,4]diazepine-5,11-dione, (S)-6-{2-[4-(4-isopropyl-piperazin-1-yl)-phenylamino]-5-trifluoromethyl-pyrimidin-4-ylamino}-3-methyl-3,4-dihydro-1H-benzo[e][1,4]diazepine-2,5-dione, (S)-3-methyl-6-{2-[4-(4-methyl-piperazin-1-yl)-phenylamino]-5-trifluoromethyl-pyrimidin-4-ylamino}-3,4-dihydro-1H-benzo[e][1,4]diazepine-2,5-dione, (S)-3-methyl-6-{2-[4-(4-prop-2-ynyl-piperazin-1-yl)-phenylamino]-5-trifluoromethyl-pyrimidin-4-ylamino}-3,4-dihydro-1H-benzo[e][1,4]diazepine-2,5-dione, (S)-6-{2-[4-(4-ethyl-piperazin-1-yl)-phenylamino]-5-trifluoromethyl-pyrimidin-4-ylamino}-3-methyl-3,4-dihydro-1H-benzo[e][1,4]diazepine-2,5-dione and methyl {(S)-2,5-dioxo-6-[2-(4-piperazin-1-yl-phenylamino)-5-trifluoromethyl-pyrimidin-4-ylamino]-2,3,4,5-tetrahydro-1H-benzo[e][1,4]diazepin-3-yl}-acetate are excluded.

2. The compound according to claim 1, wherein $R^5$ denotes halogen or —$CF_3$.

3. The compound according to claim 1 or 2, wherein
X denotes oxygen and
Y denotes —$CH_2$—.

4. The compound according to claim 1, wherein
X denotes nitrogen and
Y denotes C=O.

5. A pharmaceutically acceptable salt of a compound according to claim 1.

6. A pharmaceutical composition comprising a pharmaceutically effective amount of a compound according to claim 1, or the pharmaceutically acceptable salts thereof, in combination with conventional excipients and/or carriers.

7. The compound according to claim 1 wherein the compound is selected from one of the combinations I-1-I-16 in the table below:

| Embodiment | $R^{1'}$ | $R^2$ and $R^3$ | X and Y |
|---|---|---|---|
| I-1 | $C_{1-5}$-alkyl and m = 1 | $R^2$ denotes an optionally monosubstituted piperidinyl group | X denotes oxygen and Y - $CH_2$— |
| I-2 | $C_{1-5}$-alkyl and m = 1 | $R^2$ denotes a piperidinyl group substituted at the nitrogen | X denotes oxygen and Y - $CH_2$— |
| I-3 | $C_{1-5}$-alkyl and m = 1 | $R^2$ denotes a piperidinyl group substituted at the nitrogen by methyl, ethyl or cyclopropylmethyl | X denotes oxygen and Y - $CH_2$— |
| I-4 | $C_{1-5}$-alkyl and m = 1 | $R^2$ and $R^3$ together form an optionally mono- or polysubstituted piperazinyl group | X denotes oxygen and Y - $CH_2$- |
| I-5 | $C_{1-5}$-alkyl and m = 1 | $R^2$ and $R^3$ together denote a piperazinyl group substituted at the nitrogen | X denotes oxygen and Y - $CH_2$— |
| I-6 | $C_{1-5}$-alkyl and m = 1 | $R^2$ and $R^3$ together represent a piperazinyl group substituted at the nitrogen by methyl, ethyl, isopropyl or cyclopropylmethyl | X denotes oxygen and Y - $CH_2$— |
| I-7 | $C_{1-5}$-alkyl and m = 2 | $R^2$ and $R^3$ together form an optionally mono- or polysubstituted piperazinyl group | X denotes oxygen and Y - $CH_2$— |
| I-8 | $C_{1-5}$-alkyl and m = 2 | $R^2$ and $R^3$ together denote a piperazinyl group substituted at the nitrogen | X denotes oxygen and Y - $CH_2$— |
| I-9 | $C_{1-5}$-alkyl and m = 2 | $R^2$ and $R^3$ together represent a piperazinyl group substituted at the nitrogen by methyl, ethyl, isopropyl or cyclopropylmethyl | X denotes oxygen and Y - $CH_2$— |
| I-10 | two $R^{1'}$ together form a cycloalkyl group | $R^2$ and $R^3$ together form an optionally mono- or polysubstituted piperazinyl group | X denotes nitrogen and Y denotes C=O |
| I-11 | $R^1$ with an $R^{1'}$ forms a cyclopentyl ring | $R^2$ and $R^3$ together form an optionally mono- or polysubstituted piperazinyl group | X denotes oxygen and Y - $CH_2$— |
| I-12 | $R^1$ with an $R^{1'}$ forms a cyclopentyl ring | $R^2$ and $R^3$ together denote a piperazinyl group substituted at the nitrogen | X denotes oxygen and Y - $CH_2$— |
| I-13 | $R^1$ with an $R^{1'}$ forms a cyclopentyl ring | $R^2$ and $R^3$ together represent a piperazinyl group substituted at the nitrogen by methyl, ethyl, isopropyl or cyclopropylmethyl | X denotes oxygen and Y - $CH_2$— |
| I-14 | $R^1$ with an $R^{1'}$ forms a cyclopentyl ring | $R^2$ and $R^3$ together form an optionally mono- or polysubstituted piperazinyl group | X denotes nitrogen and Y denotes C=O |
| I-15 | $R^1$ with an $R^{1'}$ forms a cyclopentyl ring | $R^2$ and $R^3$ together denote a piperazinyl group substituted at the nitrogen | X denotes nitrogen and Y denotes C=O |
| I-16 | $R^1$ with an $R^{1'}$ forms a cyclopentyl ring | $R^2$ and $R^3$ together represent a piperazinyl group substituted at the nitrogen by methyl, ethyl, isopropyl or cyclopropylmethyl | X denotes nitrogen and Y denotes C=O | or the pharmaceutically acceptable salts thereof.

8. A method of treating a carcinoma chosen from cervical, breast, colon, head and neck, lung, pancreas, prostate, sarcomas, leukaemias, lymphomas, melanomas and gliomas comprising administering to a patient a pharmaceutically effective amount of a compound according to claim 1.

* * * * *

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: Synthetic Peptide
```

```
<400> SEQUENCE: 1

Glu Pro Leu Glu Arg Arg Leu Ser Leu Val Pro Asp Ser
1               5                   10

<210> SEQ ID NO 2
<211> LENGTH: 13
<212> TYPE: PRT
<213> ORGANISM: Artificial sequence
<220> FEATURE:
<223> OTHER INFORMATION: Synthetic Peptide

<400> SEQUENCE: 2

Glu Pro Leu Glu Arg Arg Leu Ser Leu Val Pro Lys Met
1               5                   10

<210> SEQ ID NO 3
<211> LENGTH: 28
<212> TYPE: PRT
<213> ORGANISM: Artificial sequence
<220> FEATURE:
<223> OTHER INFORMATION: Synthetic peptide

<400> SEQUENCE: 3

Leu Arg Arg Trp Ser Leu Gly Leu Arg Arg Trp Ser Leu Gly Leu Arg
1               5                   10                  15

Arg Trp Ser Leu Gly Leu Arg Arg Trp Ser Leu Gly
                20                  25
```